United States Patent [19]
Han et al.

[11] Patent Number: 5,928,645
[45] Date of Patent: Jul. 27, 1999

[54] EXTRACTED SUBSTANCE HAVING ANTI-HIV ACTIVITY

[75] Inventors: Young Bok Han; Jeong Jo Mun; Hong Ki Kyung; Jong Bae Kim, all of Seoul; Kyung Tae Kim, Kyungsangbuk-do; Hae Ri Kim; Jeong Han Kim, both of Seoul; Hyun Gil Shin, Kyungki-do; Kyung Rae Kim, Seoul; Eun Kyung Hong, Kyungki-do; Choon Won Kim, Seoul, all of Rep. of Korea

[73] Assignee: Young Bok Han & Korean Assoc. of Creation Research, Seoul, Rep. of Korea

[21] Appl. No.: 08/527,716

[22] Filed: Sep. 13, 1995

Related U.S. Application Data

[63] Continuation-in-part of application No. 08/079,608, Jun. 22, 1993, Pat. No. 5,468,487.

[30] Foreign Application Priority Data

Jun. 23, 1992 [KR] Rep. of Korea ............... 92-10894

[51] Int. Cl.⁶ .......... A61K 35/78; A61K 38/00; A61K 38/16; A61K 31/35

[52] U.S. Cl. .............. 424/195.1; 514/2; 514/8; 514/456; 514/467; 514/557; 514/558; 514/934

[58] Field of Search ............... 424/195.1; 514/2, 514/8, 456, 467, 557, 934, 558

[56] References Cited

U.S. PATENT DOCUMENTS

| 4,795,739 | 1/1989 | Lifson et al. ............... 514/8 |
| 5,141,923 | 8/1992 | Byers et al. ............... 514/12 |
| 5,178,865 | 1/1993 | Ho et al. ............... 424/195.1 |

OTHER PUBLICATIONS

Shihman, R. et al., Inhibition of growth of human immunodeficiency virus in vitro by crude extracts of Chinese medicinal herbs. Antiviral Res. 9:163–176, 1988.

Tan, G. T., et al. Evaluation of natural products as inhibitors of human immunodeficiency virus type 1 (HIV–1) reverse transcriptase. J. Nat. Prod. 54(1):143–154, 1991.

*Primary Examiner*—John W. Rollins
*Attorney, Agent, or Firm*—Birch, Stewart, Kolasch & Birch, LLP

[57] ABSTRACT

The present invention provides a extracted substance from a mixture of a non-fat starch from *Ricini semen* and a root of coptis Sp. This substance is suitable for use in the therapeutic applications of AIDS.

12 Claims, 29 Drawing Sheets

FIG. 7

FILE NAME : RICIN

CREATED : 14:08
DATA : ORIGINAL

MEASURING MODE : ABS.
SCAN SPEED : FAST
SLIT WIDTH : 1.0
SAMPLING INTERVAL : 0.2

PEAK PICK

| NO. | WAVELENGTH (nm) | ABS. |
|---|---|---|
| 1 | 464.80 | 0.031 |
| 2 | 450.40 | 0.043 |
| 3 | 435.20 | 0.045 |
| 4 | 393.40 | 0.051 |
| 5 | 371.00 | 0.055 |
| 6 | 361.40 | 0.057 |
| 7 | 357.60 | 0.062 |
| 8 | 346.60 | 0.065 |
| 9 | 339.20 | 0.066 |
| 10 | 303.00 | 0.118 |
| 11 | 255.80 | 0.159 |

FILE NAME : RICB

CREATED : 13:55
DATA : ORIGINAL

MEASURING MODE : ABS.
SCAN SPEED : MEDIUM
SLIT WIDTH : 1.0
SAMPLING INTERVAL : 0.2

PEAK PICK

| NO. | WAVELENGTH (nm) | ABS. |
|---|---|---|
| 1 | 421.00 | 0.498 |
| 2 | 343.00 | 2.356 |
| 3 | 341.00 | 2.363 |
| 4 | 262.80 | 2.639 |

FIG. 23

```
┌──────┐
│ ric  │──── saturated with ammonium sulfate solution(70%) ────┐
└──┬───┘                                                        │
   │                                                            │
┌──┴─────────┐                                            ┌─────┴────┐
│ precipitate│                                            │ solution │
└──┬─────────┘                                            └──────────┘
   │ dialysis
   │ freeze drying
┌──┴──────┐
│ protein │
└─────────┘
```

Amino Acid Analysis Chromatogram of Standard

FIG. 26 Amino Acid Analysis Chromatogram of the extract

Schematic flow diagram of N(O,S)-isobutyloxycarbonylation, solid-phase extraction and tert-butyldimethylsilylation for amino acid standards Schematic flow diagram of N(O,S)-isoBOC reaction, solid-phase extraction and TBDMS derivatization of amino acids from the extract Schematic flow diagram of solid-phase extraction and TBDMS derivatization of organic acids from the extract Fractionation of the extracted substance by solvent extraction.

EXTRACTED SUBSTANCE HAVING ANTI-HIV ACTIVITY

This application is a continuation-in-part of application Ser. No. 08/079,608 filed on Jun. 22, 1993, now U.S. Pat. No. 5,468,487 the entire contents of which are hereby incorporated by reference.

BACKGROUND OF THE INVENTION

1. Field of the Invention

The present invention relates to a novel extracted substance useful for inhibition of the human immunodeficiency virus (HIV) and a process for extracting the same. Specifically, the extract is prepared from a mixture of a non-fat starch from *Ricini semen* and a root of Coptis which exhibits a suitable anti-HIV activity.

2. Description of the Prior Art

All references of the scientific and patent literature cited herein are hereby incorporated in their entirety by reference by such citation.

In 1983, it was found that HIV-1 is the causative agent of acquired immunodeficiency syndrome (AIDS). Thereafter, the genome of the virus was cloned and several approaches to discover inhibitors of HIV have been followed.

The selective infection of helper T cells (TH) by HIV induces a disorder of the immune system and subsequently results in AIDS. The reverse transcribed viral genome usually remains in the chromosome of host cells in the latent period. At the end of the latent period, viral proliferation induces cell fusions that produce syncytia, and subsequently kill cells by an acute infection. In the absence of syncytium formation, the viral proliferation continues in a chronic infection, without any significant cytopathic effects.

The membrane protein gp 120 of the virus recognizes CD4 receptors present in host cells; the virus binds to the CD4 receptor through this recognition event. The virus enters cells and subsequently copies its RNA genome into a DNA copy using a reverse transcriptase. The reverse transcribed viral genome then integrates into the chromosomal DNA of host cells.

The viral genome is replicated in the cells by several signals and factors required for host cell proliferation. Viral proteins are then produced, a process which requires the action of trans-acting regulatory proteins encoded by the viral genome. Post-translational processing of the viral proteins for assembly of complete virus particles involves the action of an HIV-specific protease and also glycosylation of some viral proteins.

Accordingly, in order to develop anti-HIV drugs, inhibitors of the following functions of the viral replication cycle should be developed as chemotherapies.

(a) inhibition of interactions between gp120 of the virus and CD4 receptors of host cells, (b) inhibition of the action of reverse transcriptase in changing RNA of the virus into proviral DNA, (c) inhibition of activities of viral regulatory proteins, (d) inhibition of cleavage of viral precursor proteins, (e) inhibition of an action of a glucosidase or a mannosidase for a prevention of glycosylation of viral proteins and so forth.

A number of drugs having selective anti-viral efficacy have hitherto been developed using differences between HIV and human host cells. Such drugs, especially drugs inhibiting viral proliferation, include dextran sulfates and peptide T having an inhibitory function of (a) described above; dideoxycytidines, dideoxyinosines and phosphonoformates having a function of (b). Beside these are the examples of ribavirin, castanospermine, GLQ 223, antisense oligonucleotides, protease inhibitors, and so forth. However, these drugs are still not commercially available for AIDS.

In addition, zidovudine (azidothymidine, AZT) is currently used as a medicine for AIDS, but has serious disadvantages in that it usually induces side effects including symptoms such as headaches, emesis, high fevers, injury of the hematopoietic system and nervous system, and suppression of the liver function. Also resistance to AZT is often found in long-term therapy.

We, the inventors of the present invention, have intensively conducted a wide range of experiments in order to develop potent HIV inhibitors having good therapeutic effects. As a result, we have discovered that a novel extracted substance isolated from *Ricini semen* and a root of Coptis has significantly improved anti-HIV activity, and could provide a good therapy for HIV infection.

SUMMARY OF THE INVENTION

It is therefore an object of the invention to provide a novel extracted substance which is useful as an inhibitor of HIV proliferation.

It is still another object of the invention to provide a therapeutic composition comprising, as an active ingredient, the novel extracted substance of the present invention, in admixture and in association with conventional ingredients, such as carriers, excipients, extenders, and so forth.

It is a still further object of the invention to provide a method for treating AIDS by using the novel extracted substance of the present invention.

Any additional objects of the invention will become apparent through reading the remainder of the specification.

BRIEF DESCRIPTION OF DRAWINGS

FIG. 7 represents UV spectrum of the extract from *Ricinus communis* L.

FIG. 23 represents protein isolation from the extract by a salt precipitation method.

DETAILED DESCRIPTION OF THE INVENTION

Figure 1:
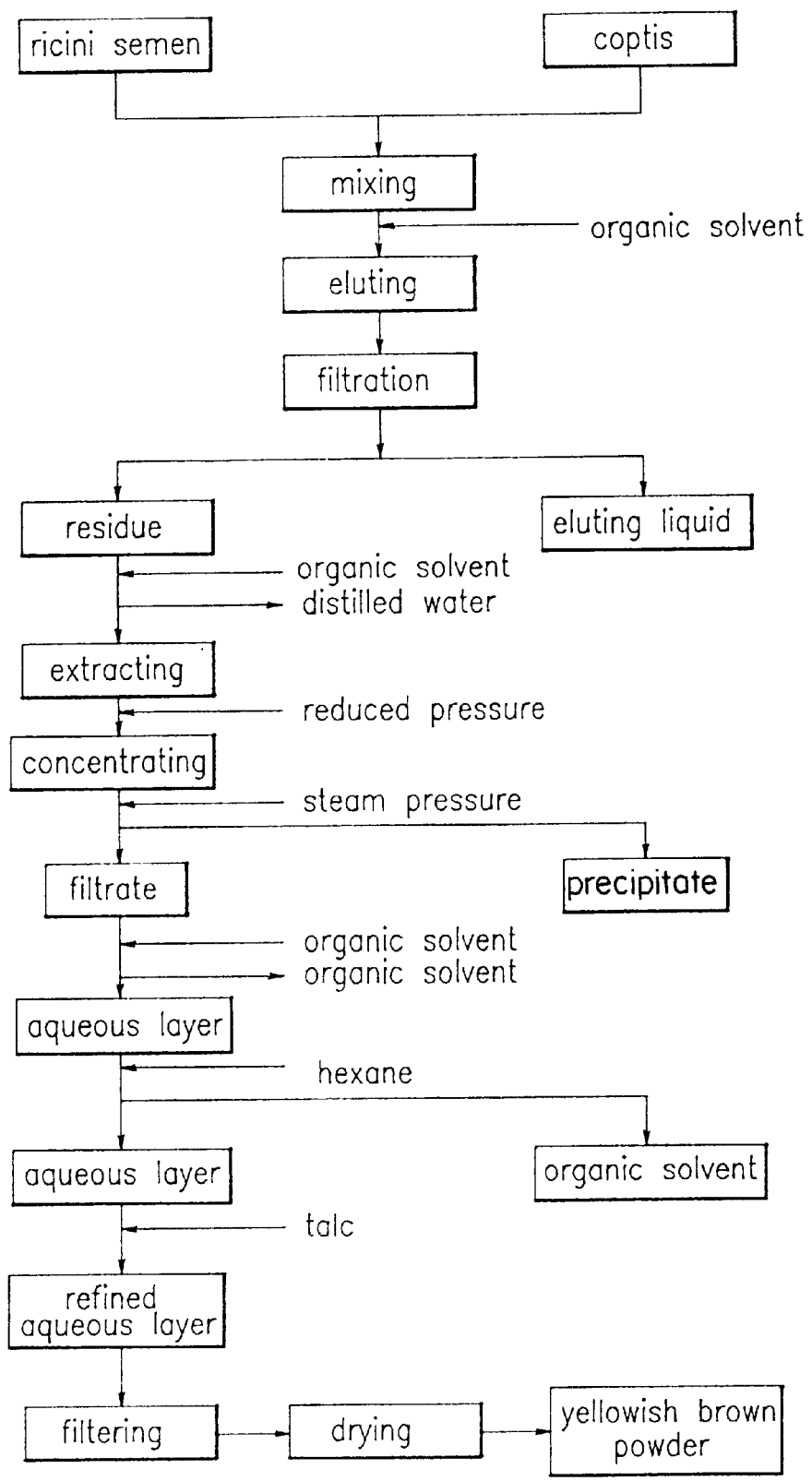
FIG. 1 is a diagram showing an extraction process for a product according to the invention.
Figure 2:
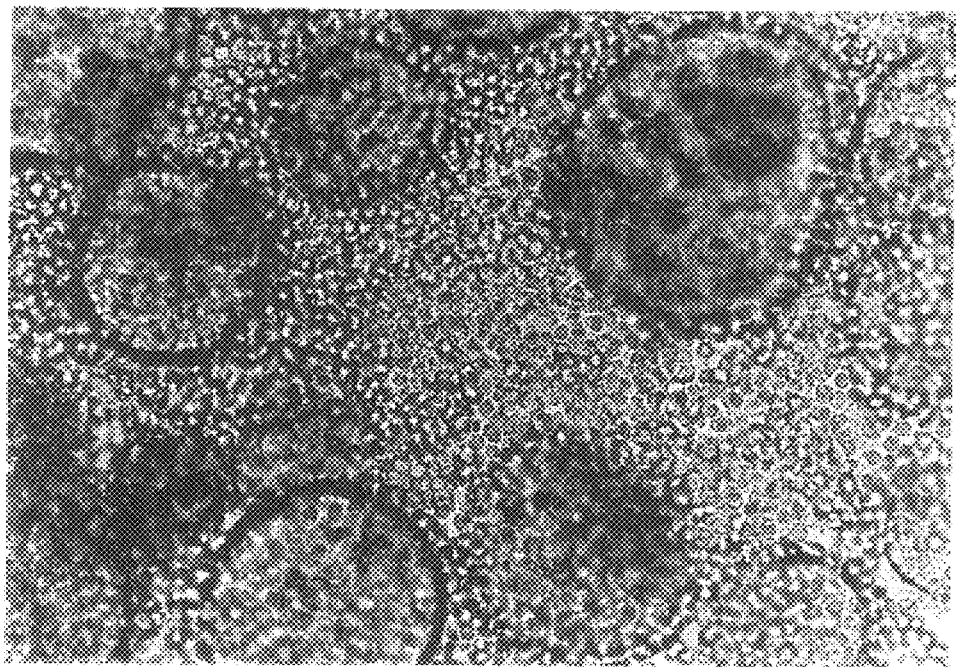
FIG. 2 represents a microphotograph of HIV infected cells used as a control in experiments demonstrating the invention.

According to the present invention, a novel extract isolated from *Ricini semen* and a root of Coptis sp. is provided.

The present invention resides partly in an extract from a mixture of the non-fat starches of *Ricini semen* and a root of a Coptis species, wherein said extract comprises berberine and at least one flavanoid, and wherein said extract is substantially free of the protein ricin and the alkaloid ricinine.

The composition preferably further comprises a protein component of molecular weight approximately 10 kilodaltons as measured by electrophoresis. The protein component is comprised primarily of the amino acids glycine, pyroglutamic acid, glutamic acid, asparagine, serine, homoserine, and aspartic acid.

In the protein component of the extract, a preferred ratio of aspartic acid to asparagine to glutamic acid, to serine to pyroglutamic acid to homoserine to glycine is 100:17.8:8.7:3.3:2.6:1.2:1.2.

The extract of the invention further comprises the organic acids malic acid, ferulic acid, fumaric acid and succinic acid as organic acids present in a high proportion of the organic acid fraction. The extract further comprises the organic acids protocatechuic acid, vanillic acid, lactic acid, palmatine, glycolic acid, stearic acid, syringic acid, cis-aconitic acid and methylsuccinic acid as organic acids present in lower proportions of the organic acid fraction. A preferred ratio of malic acid to ferulic acid to fumaric acid to succinic acid in the composition is 100:82.3:81.1:34.8. A most preferred embodiment of the extract of the invention is one wherein the ratio of malic acid to ferulic acid to fumaric acid to succinic acid to protocatechuic acid to vanillic acid to lactic acid to palmatine to glycolic acid to stearic acid to syringic acid to cis-aconitic acid to methylsuccinic acid is 100:82.3:81.1:34.8:17.8:13.1:9.6:9.3:7.5:7.2:3.9: 3.1:2.5.

The extracted substance according to the invention is suitable to inhibit a certain step during the viral replication cycle, and it exhibits higher activity as an HIV proliferation inhibitor than other conventional inhibitors.

The extracted substance of the present invention is derived from a mixture of a non-fat starch from *Ricini semen* and a root of Coptis sp. The mixing ratio of *Ricini semen* and Coptis sp. is preferably from 2:5 to 5:2. Toxic components such as the protein ricin and the alkaloid ricinine, which may present in the mixture, are removed from the extract of the present invention by a process depicted in FIG. 1.

The *Ricini semen* used in the invention comprises 30 to 50% of fats. It also contains proteins such as globulin, nucleoalbumin, glycoprotein, ricin, lipase, etc., and a toxic alkaloid ricinine. It originated from India and tropical Africa, and is widely distributed except in the cold latitudes. *Ricini semen* is largely cultivated in the northeastern districts of Asia and is plentiful in America and Java. It grows mainly as a shrub in the tropics and the subtropics and as an annual herb in the temperate latitudes. A representative example of the *Ricini semen* is *Ricinus communis* L.

The Coptis sp., the other plant used in the invention, is a perennial herb which is naturally grown or cultivated in hillocks of many countries in Asia. Examples are Chinese species such as *Coptis chinensis* (FRANCH), *Coptis deltoidis* (C. Y. CHENG et al), *Coptis quinquesecta* (W. T. WANG), *Coptis teetoide* (C. Y. CHENG) and *Coptis chinensis* (FRANCH) var. *brevisepala* (W. T. WANG et al), Indian and Nepalese species such as *Coptis teeta* (WALL), Japanese species such as *Coptis japonica* (MAKINO) var. dissecta (NAKAI), *Coptis japonica* (MAKINO) var. *japonica* (SATAKE), Korean species such as *Jeffersomia dubia* (BENTHAN and HOOKER), and so forth. The yellow or yellowish-brown components of Coptis sp. roots consist mainly of alkaloid berberines, and contain palmatines, rateorrhizins, captisins, magnoflorines, etc. These components are considered to have activity in stimulating bile and pancreatin secretion, to prevent atherosclerosis, and to have antiphlogistic activity. Thus, the Coptis sp. is clinically used as an antiphlogistic agent and for treatment of hyperemia and inflammation.

The extracted substance of the invention is obtained by extraction of a mixture of said *Ricinus communis* L and Coptis sp. roots. In case of a separate extraction of each root, the extract has a severe side effects and poor anti-HIV activity.

Referring now to FIG. 1, a diagram showing an extraction process for a product according to the invention, the novel extracted substance of the invention can be prepared by a process which comprises the steps of:

(a) mixing a non-fat starch from *Ricinus communis* L and a root of Coptis sp. in a weight ratio of 2:5 to 5:2, most preferably 4:5 to 5:4;

(b) extracting the mixture with an organic solvent, preferably one or more fatty acid esters, but most preferably chloroform or hexane, at a temperature of 20 to 25° C. for 20 to 25 hours;

(c) subjecting the resulting extract to repeated filtration under reduced pressure to carry out separation from the residue;

(d) drying the residue to remove the organic solvent, and then adding about 5,000 mL of distilled water thereto;

(e) extracting the resulting dried residue by heating at 100° C. for 3 to 4 hours;

(f) concentrating the resulting aqueous extract under reduced pressure to 1,500 mL, and then removing the precipitates;

(g) adding chloroform to the remaining aqueous extract, followed by agitating the mixture and separating the aqueous and organic phases;

(h) removing the chloroform phase and further extracting the aqueous phase with hexane to remove any remaining organic solvent;

(i) refining the aqueous phase with a talc and subjecting the resultant to filtration under a reduced pressure to give a filtrate; and (j) filtering the filtrate through a membrane filter to give a second filtrate and then lyophilizing the second filtrate to give yellowish brown powders.

Fat and fat-soluble components were removed by extraction with chloroform and hexane at a temperature of 20–25° C. for 20–25 hours. The organic solvent was removed by using a rotatory evaporator. After adding 5 L of distilled water, water-soluble components of *Ricinus Communis L.* were extracted at 100° C. for 3–5 hours. After cooling the extract, the extract was filtered and the precipitates were removed. The extract was lyophilized.

As the solvent to be used in step (b) above, one or more solvents selected from the group consisting of aliphatic hydrocarbons, aromatic hydrocarbons, alcohols, $C_1$–$C_8$ halohydrocarbons comprising 1 to 6 of the same or different halogen atoms, esters of a fatty acid comprising methyl, ethyl, propyl, butyl or amyl, acetic acid esters, and ketones having $C_1$–$C_8$ aliphatic or aromatic groups may be used.

The extracted substance does not contain any toxic components such as the protein ricin or the alkaloid ricinine. The extracted substance according to the invention may be administered to humans by means of various types of injection, for example, intravenous, intramuscular, subcutaneous and intraperitoneal injection. Preparations for injection are formulated by dissolving the extract of the present invention in distilled water or physiological saline.

In further aspect, the present invention provides a composition for use in treating AIDS, which comprises, as an active ingredient, the novel extracted substance of the invention, in mixture or in association with conventional ingredients such as carriers, excipients, and other additives.

In still another aspect, the present invention provides a method for treating AIDS which comprises administering the novel extracted substance of the present invention to a subject.

DESCRIPTION OF THE PREFERRED EMBODIMENTS

The present invention will be illustrated in greater detail by way of the following examples. The examples are presented for illustration purpose only and should not be construed as limiting the invention which is properly delineated in the claims.

EXAMPLE 1

Preparation of the Extract from Roots of Coptis sp. and *Rincini semen*

This example illustrates preparation of the extract of the present invention from a mixture of dried and powdered roots of Coptis sp. and *Ricini semen*.

The novel extract of the invention was prepared by the steps of:

(a) removing fat and fat-soluble components of *Ricinus communis* root by extraction with chloroform and hexane at a temperature of 20–25° C. for 20–25 hours;

(b) removing the organic solvent by rotatory evaporator. After adding 5 L of distilled water, water-soluble components of *Ricinus communis* L. was extracted at 100° C. for 3–4 hours;

(c) cooling the extract, then filtering the extract;

(d) removing the precipitates, then lyophilizing the extract;

(e) mixing dried and powdered Coptis and *Ricinus communis* in a weight ratio of 1:1;

(f) extracting the mixture with chloroform and hexane at a temperature of 20–25° C. for 20–25 hours;

(g) removing the organic solvent by rotatory evaporator. After adding 5 L of distilled water, water-soluble components of *Ricinus communis* L. was extracted at 100° C. for 3–4 hours;

(h) concentrating the resulting aqueous extract under reduced pressure to 1,500 ml, and then filtrating the extract;

(i) removing the precipitates, then adding chloroform to the remaining aqueous extract, followed by removing the chloroform layer using a rotatory evaporator;

(j) further extracting the aqueous phase with hexane to remove the fat-soluble component;

(k) lyophilizing the extract.

EXAMPLE 2

In Vitro Assay

To evaluate toxicity of the extracted substances on a T cell line (SupT1), maximum acceptable concentrations of antiviral agents were determined as follows:

A solution containing the extract of the invention in several concentrations, from 1.0 ppm to 100 ppm as shown in Table 1, was added to 5 to $8 \times 10^5$ test cells and the treated cells were incubated. After incubation, the cells were treated with trypan blue. The number of cells that excluded the dye was counted using a hemocytometer. "$TCID_{50}$" is defined as the 50% tissue culture-infective dose. (Reference: Techniques in HIV research, ed. Aldovini, A., and Walter, B. D., Stockton Press, N.Y. Unitd States, Chapter 4. Quantitative assay for virus infectivity, pp. 71–73, 1990.) The 50% tissue culture-infective dose ($TCID_{50}$) is calculated using the method of Reed and Muench (Dulbecco, R., "Endpoint Method-Measurement of the infectious titer of a viral sample" in the chapter entitled: The Nature of Viruses in Virology, Second Edition, J. P. Lippincott, Philadelphia, pp. 22–25, 1988). This method is applicable for measuring the infectious titer of a viral sample from an assay involving a series of progressive dilutions of virus. To generate the 50% endpoint dilution, an empirical pooling of the results is done after reading the plate for visible infection at all of the dilutions tested. In cell cultures, the tissue culture infective dose ($TCID_{50}$) is the dilution of virus suspension that infects 50% of the cell cultures as measured by visible CPE.

After a three-day incubation the number of multinucleate cells in each culture were counted. As comparative tests, similar experiments were performed using AZT or berberine, rather than the extract of the present invention, to treat the cells. The results of these experiments are shown in Tables 1 through 3.

The effect of the extract of the present invention on reverse transcriptase activity and on viral replication was also measured in H9 host cells. HIV infected H9 cells were cultured in RPMI 1640 supplemented with 10% (v/v) of heat-inactivated fetal calf serum and 1% (v/v) penicillin-streptomycin. $2.5 \times 10^5$ H9 cells were infected with native HIV in the absence and presence (2.0 μg/ml, 5.0 μg/ml) of the extract in a 24 well plate. Every third day ¼ of the cultures were transferred to new media containing the same concentration of the extract. The cultures were harvested after 9 days and centrifuged for 3 minutes in an Eppendorf centrifuge. 600 μl of supernatant was mixed 300 μl of 30% polyethylene glycol (PEG) and then centrifuged for 10 minutes. The pellet was resuspended in RT suspension buffer (50 mM Tris, pH 7.5, 1 mM DTT, 20% glycerol, 0.25% Triton X-100). These virus samples were frozen at −70° C. until assayed. Aliquots of virus (10 μl) were incubated with 20 μl of a cocktail containing 50 mM Tris, pH 7.5, 5 mM DTT, 5 mM $MgCl_2$, 150 mM KCl, 0.05% Triton X-100, 0.3 mM glutathione, 0.5 mM EGTA, 50 μg/ml poly(rA)dT, 10μ Ci thymidine triphosphate, and 17.25 μl distilled water for 1 hour at 37° C. (Hoffman et al., Characterization of the AIDS-associated retrovirus reverse transcriptase and optimal conditions for its detection in viruses. Virology 147, 326–335, 1985.) Reactions were stopped by placing the tubes on ice and adding 2 ml of ice-cold pyrophosphate (0.01M in 1N HCl) and 2 ml of ice-cold 10% trichloroacetic acid (TCA). Precipitates were collected on Whatman GF/C glass fibers, washed several times with ice-cold 5% TCA and once with 70% ethanol, air dried and counted in a liquid scintillation counter.

Figure 3:
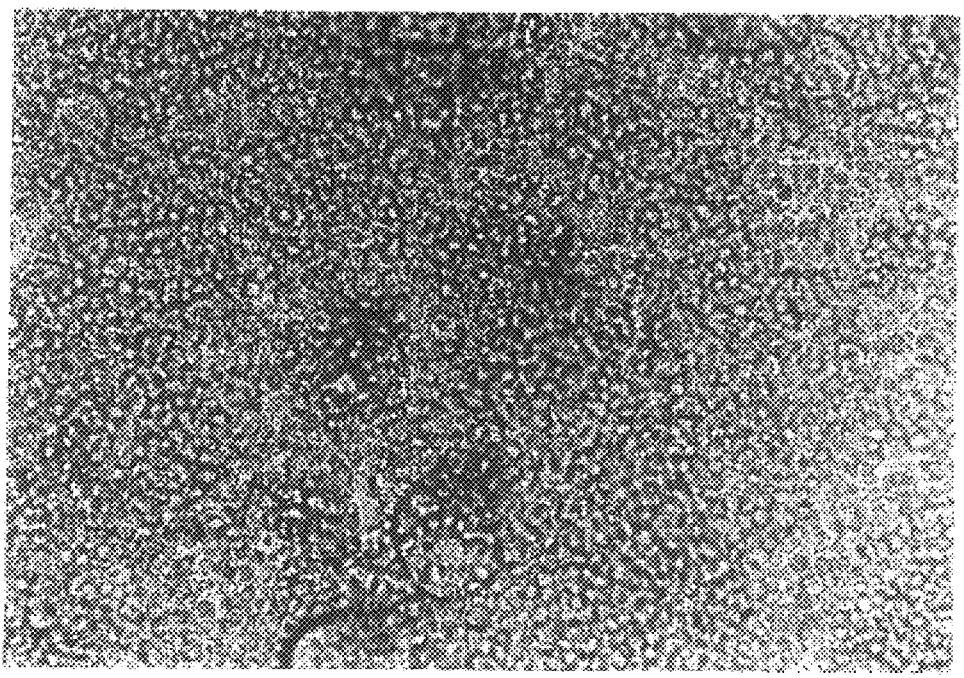
FIG. 3 represents a microphotograph of HIV-infected cells to which 10 $\mu$g/ml of the extract of the invention was administered.
Figure 4:
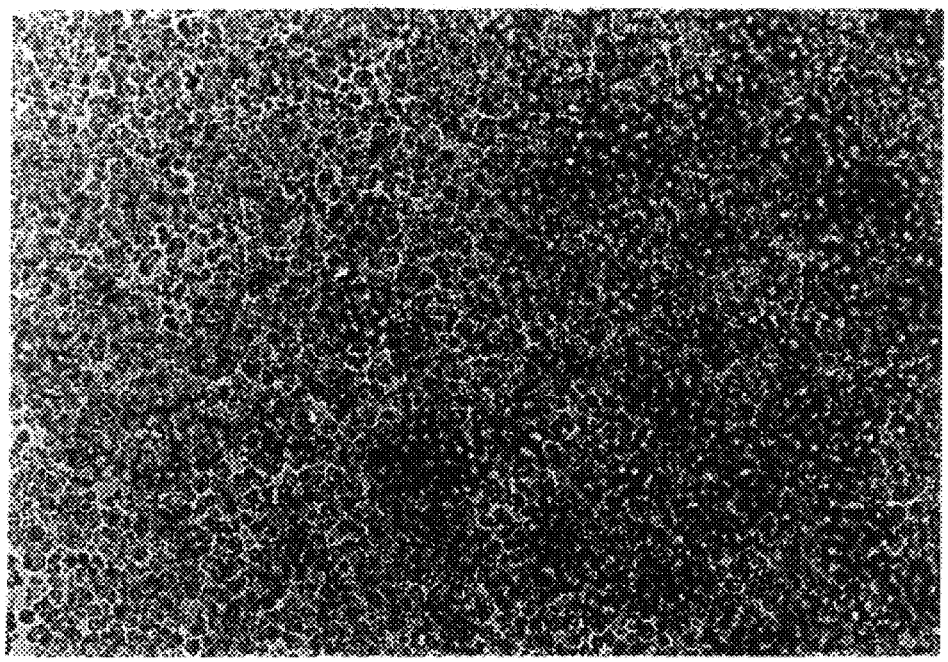
FIG. 4 represents a microphotograph of HIV-infected cells to which 50 $\mu$g/ml of the extract of the invention was administered.
Figure 5:
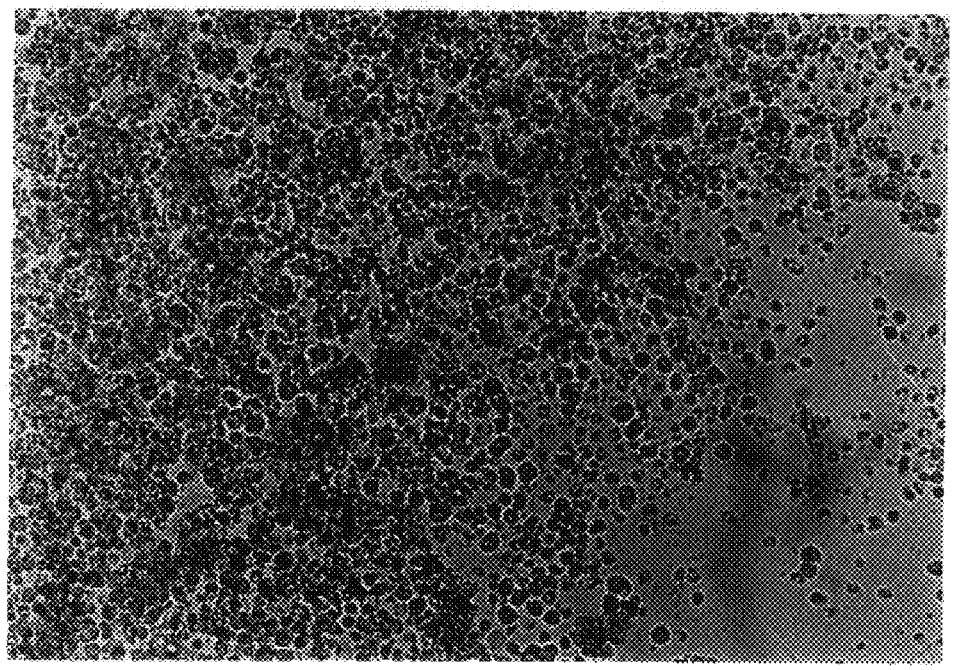
FIG. 5 represents a microphotograph of HIV-infected cells to which 100 $\mu$g/ml of the extract of the invention was administered.

Tables 1–3 and FIGS. 3 through 5 show the results of the syncytium-formation assays. In Tables 1–3 and FIGS. 3–5, it can be seen that multinucleate cells are not observed at a concentration of 10 μg/mL or more. The extract of the invention is inferior to AZT as to its ability to inhibit syncytium formation inhibition at those concentrations that are comparable. However, AZT induces serious side effects such as headaches, emesis of several parts of the body and high fibrosis during long-term administration. Thus, the finding that the extract of the present invention can inhibit syncytium formation with low toxicity is significant.

TABLE 1

| | The extract of the Invention | | | | |
|---|---|---|---|---|---|
| Conc. (μg/mL) | 0 | 1 | 10 | 50 | 100 |
| No. of Multiple-Nucleate Cells | 9 | 3 | 0 | 0 | 0 |
| Toxicity on the Host Cells | 0% | 0% | 20% | 30% | 40% |

TABLE 2

| | AZT | | | | |
|---|---|---|---|---|---|
| Conc. (μg/mL) | 0 | 0.5 | 0.2 | 1 | 5 |
| No. of Multiple-Nucleate Cells | 8 | 1 | 0 | 0 | 0 |
| Toxicity on the Host Cells | 0% | 0% | 0% | 0% | 0% |

TABLE 3

| | Berberine | | | | |
|---|---|---|---|---|---|
| Conc. (μg/mL) | 0 | 0.1 | 0.5 | 1 | 3 |
| No. of Multiple-Nucleate Cells | 9 | 8 | 5 | 2 | 1 |
| Toxicity on the Host Cells | 0% | 0% | 0% | 0% | 10% |

Figure 6:
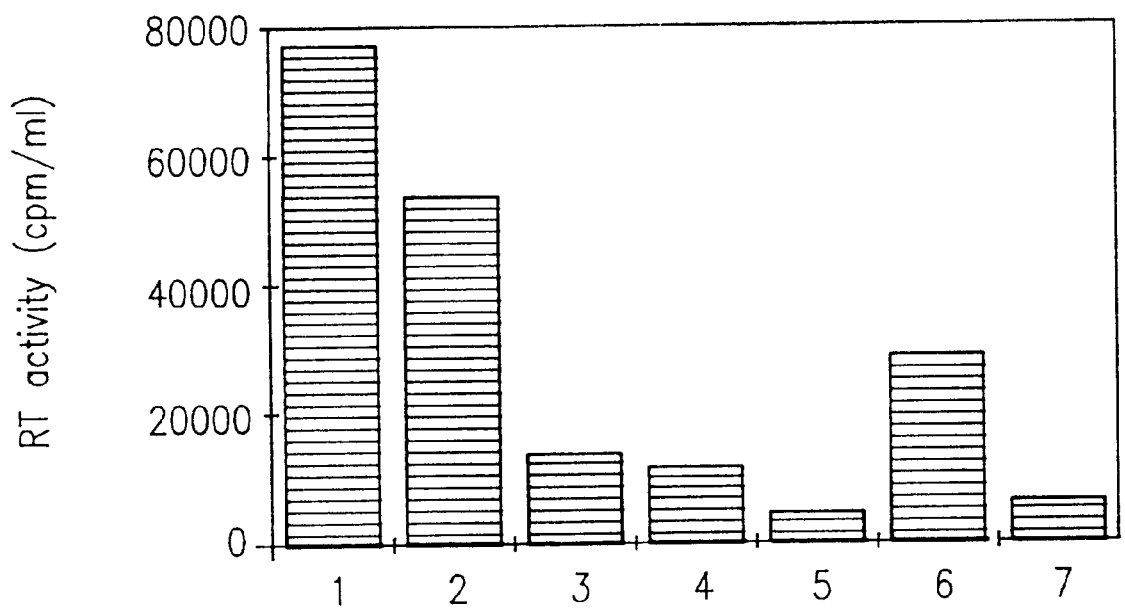
FIG. 6 represents the effect of the extract on the reverse transcriptase activities of HIV infected H9 cells, 1=control, 2=AZT at 0.05M, 3=AZT at 0.2, 4=extract of the invention at 2 $\mu$g/ml, 5=extract of the invention at 5 $\mu$g/ml, 6=berberine at 0.1 $\mu$g/ml, 7=berberine at 0.5 $\mu$g/ml.

FIG. 6 shows the effect of the extract on the reverse transcriptase activity from HIV-infected H9 cells. The extract of the present invention 2.0 μg/ml showed significant inhibition of viral RT activity. Berberine at 0.5 μg/ml also had marked inhibitory effect on RT activity. AZT at 0.2 μM, as a positive control, showed comparable activity with the above concentrations of the extract and berberine.

EXAMPLE 3

Cytotoxicity and Anti-HIV Effect of the Extract

Anti-HIV effect of the extract of the present invention was investigated according to the Screening Method of the National Cancer Institute (USA) utilized for surveying natural products for compounds having anti-HIV effect.

This experiment is to test anti-HIV effect by measuring the capability of the test material in protecting T-cells from killing by HIV-1.

Cells of the CEM-SS T-leukemia cell line (cloned cell line from CEM cell line; NCI) and HIV-1 Rf were used for the experiment The CEM-SS T-leukemia cell line (cloned cell line from CEM cell line; NCI) is easily infected with HIV, and dies 100% by virus infection. CEM-SS cells form multinuclear giant cells upon HIV infection. CEM-SS T-leukemia cells were cultured in RPMI 1640 with 10% fetal bovine serum at 37° C., under a 5% $CO_2$ atmosphere. The extract of the present invention was dissolved in DMEM supplemented with 0.1% DMSO (DimethylSulfoxide) and 10% FBS. The extract was serial diluted from 2000 μm/ml.

The antiviral effect of the extract of the present invention was investigated as follows. $3 \times 10^5$ CEM-SS cells were infected with HIV-1, strain Rf (MOI—0.1, host cell: virus—10:1), then the extract of the present invention was added. HIV-1 Rf was isolated from a patient with AIDS and cultured in H9 cells.

Anti-HIV effect of the extract was determined by measuring viability of the cells protected from killing by HIV-1 killing by the extract. The cell viability was measured by the XTT tetrazolium salt: 2, 3-bis (2-methoxy-4-nitro-5-sulfophenyl)-{(phenylamino) carbonyl}-2H-tetrazolium hydroxide) method (Weislow, O. S., Kiser, R., Fine, D. L., Badar, J., Shoemaker, R. H., and Boyd, M. R.: New soluble-formazan assay for HIV-1 cytopathic effects: Application to high-flux screening of Synthetic and natural products for AIDS-antiviral activity. J. N. C. I. vol. 81 (8) p577–586, 1989.). The XTT method is to quantitate the activity of a mitochondrial enzyme, which is directly related to the viability of the cells. XTT makes soluble XTT formazan when decomposed by a mitochondrial enzyme. The content of soluble XTT formazan is dependent upon the cell viability. The absorbance (OD) as measured by ELISA reader at 450 nm represents cell viability.

Anti-HIV effect was evaluated by $IC_{50}$ and $EC_{50}$. $IC_{50}$ was obtained from uninfected control CEM-SS cells by treatment with the extract of the present invention at various concentrations. "$IC_{50}$" means the concentration at which the extract exhibits 50% inhibition of the host cells. It represents cytotoxicity of the extract of the present invention. To determine $EC_{50}$, HIV-infected cells were treated by the extract of the present invention. "$EC_{50}$" means the concentration at which the extract exhibits 50% protective effect of the host cells from death by HIV infection.

The difference between $IC_{50}$ and $EC_{50}$ of the extract is high when the extract has low cytotoxicity and high anti-HIV effect. That is, selectivity of the extract is high when the ratio of $EC_{50}$ to $IC_{50}$ is high.

$IC_{50}$ of the extract of the present invention was $2.97 \times 10^2$ $\mu$m/ml, and $EC_{50}$ was 0.01 $\mu$g/ml. The extract of the present invention showed low cytotoxicity, and excellent anti-HIV effect, i.e. high selectivity.

EXAMPLE 4

Characteristics of the Extract of the Present Invention

Figure 8:
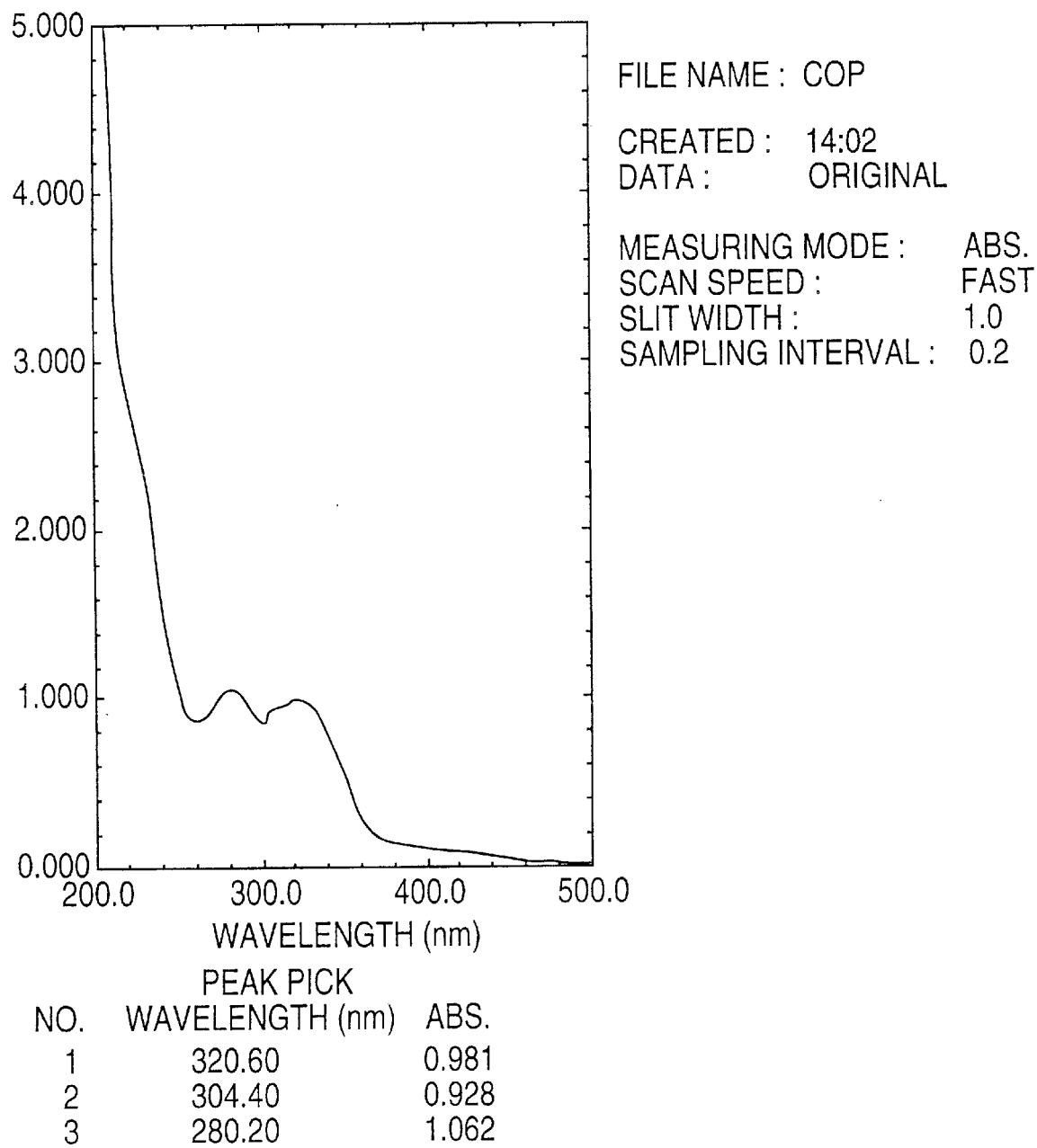
FIG. 8 represents UV spectrum of the extract from coptis.
Figure 9:
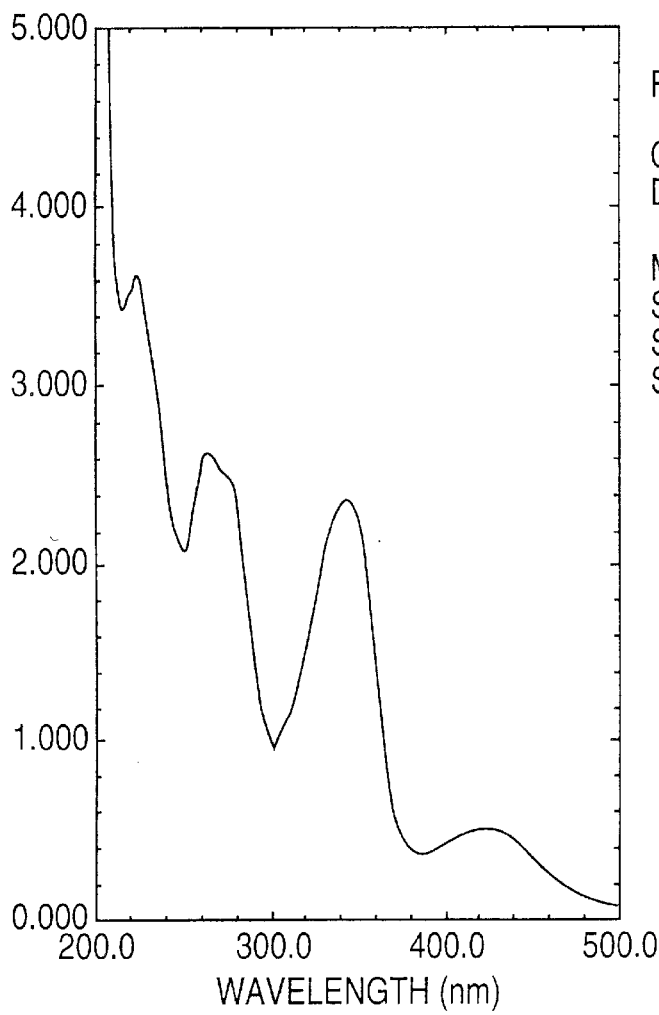
FIG. 9 represents UV spectrum of the extract of the present invention.

The extract and components of the extract of the present invention, namely *Ricinus communis* L. and Coptis were investigated by UV scanning (Shimazu, Japan) and HPLC (Waters). FIG. 7 shows the UV scanning profile of the extract from *Ricinus communis* L. FIG. 8 shows the UV scanning profile of the extract from Coptis. FIG. 9 shows the UV scanning profile of the extract of the present invention. UV scanning profile of the extract was very different from the other profiles.

Figure 10:
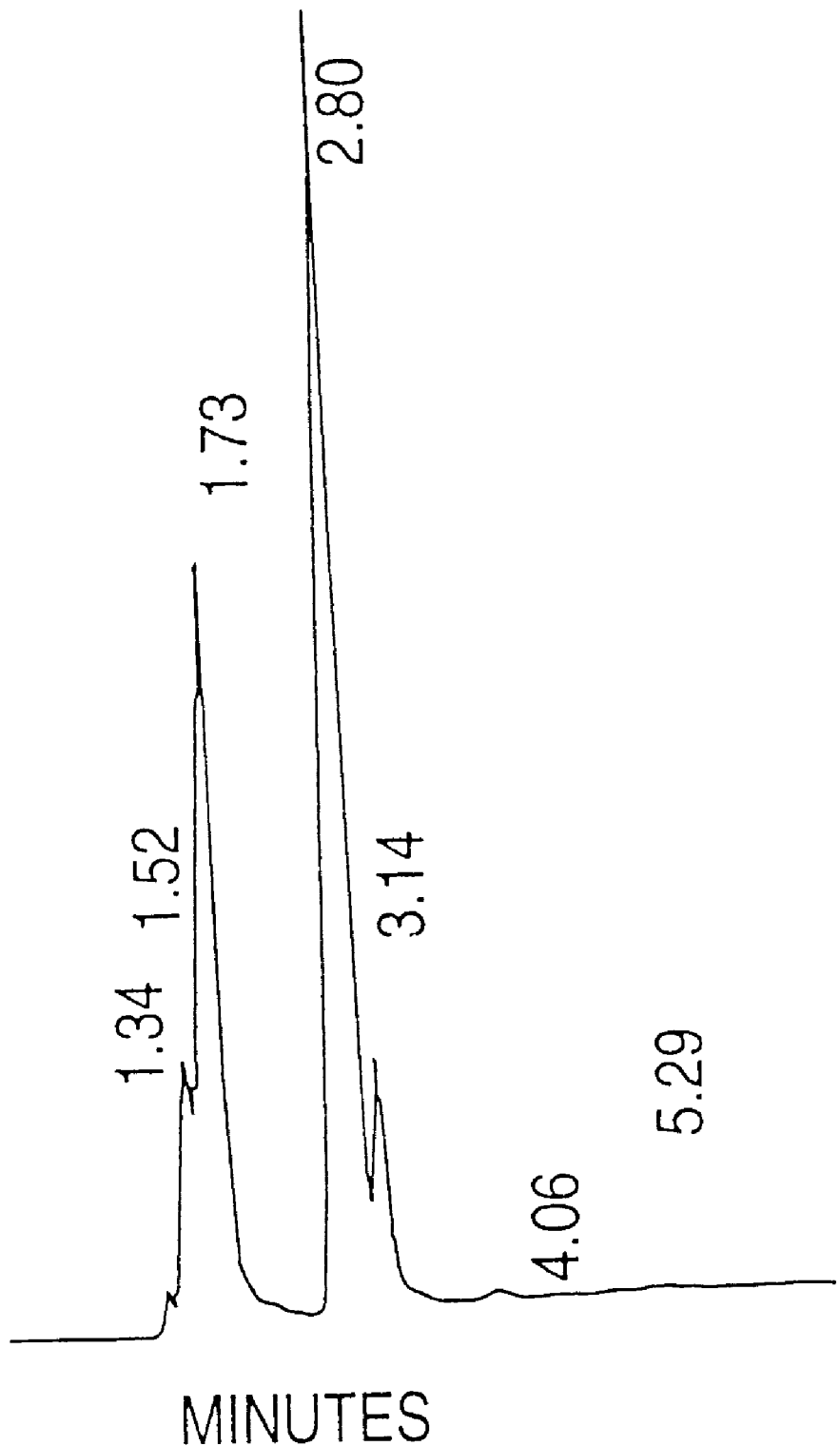
FIG. 10 represents a HPLC profile of the extract from *Ricinus communis* L.
Figure 11:
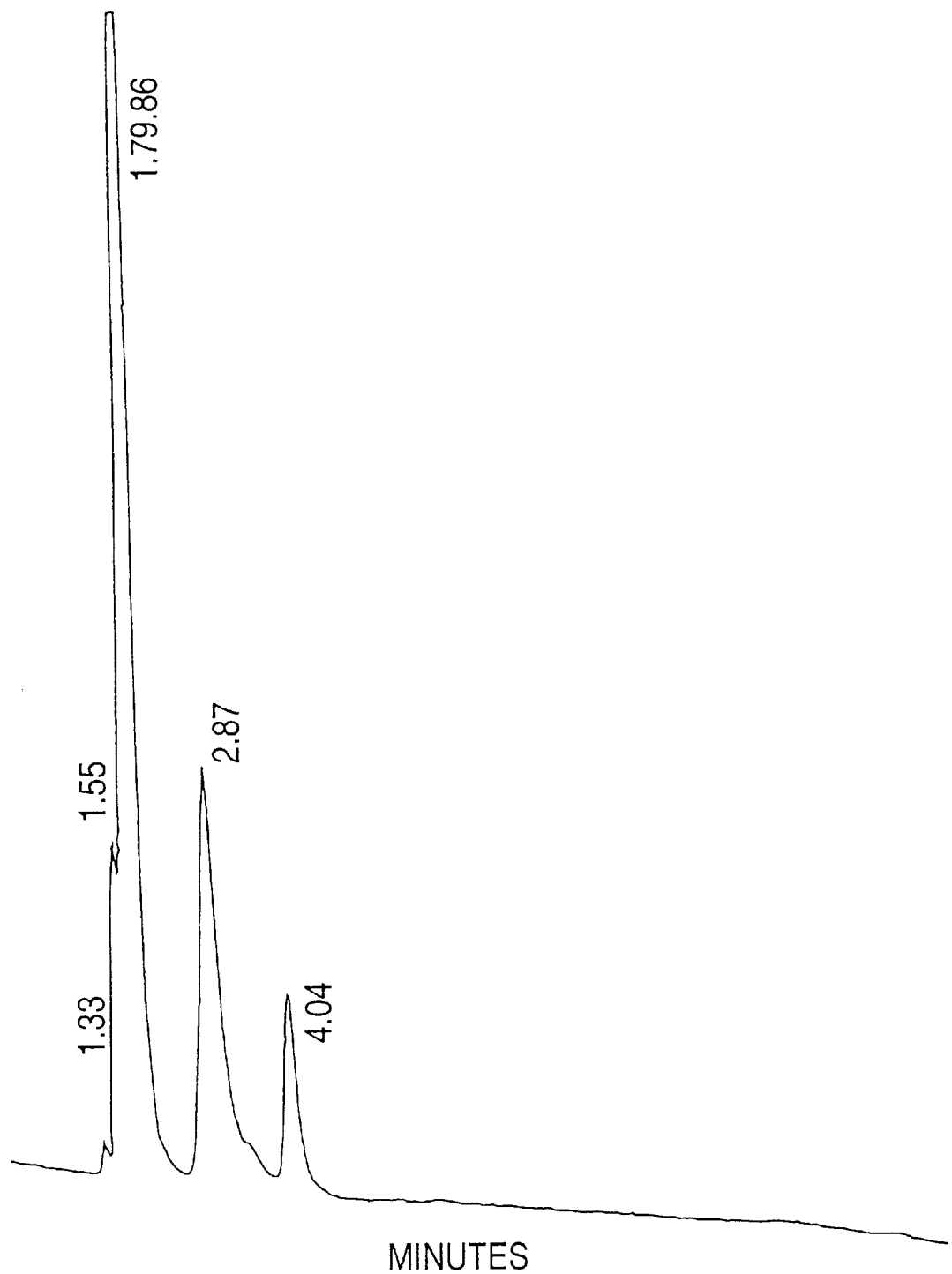
FIG. 11 represents a HPLC profile of the extract from coptis.
Figure 12:
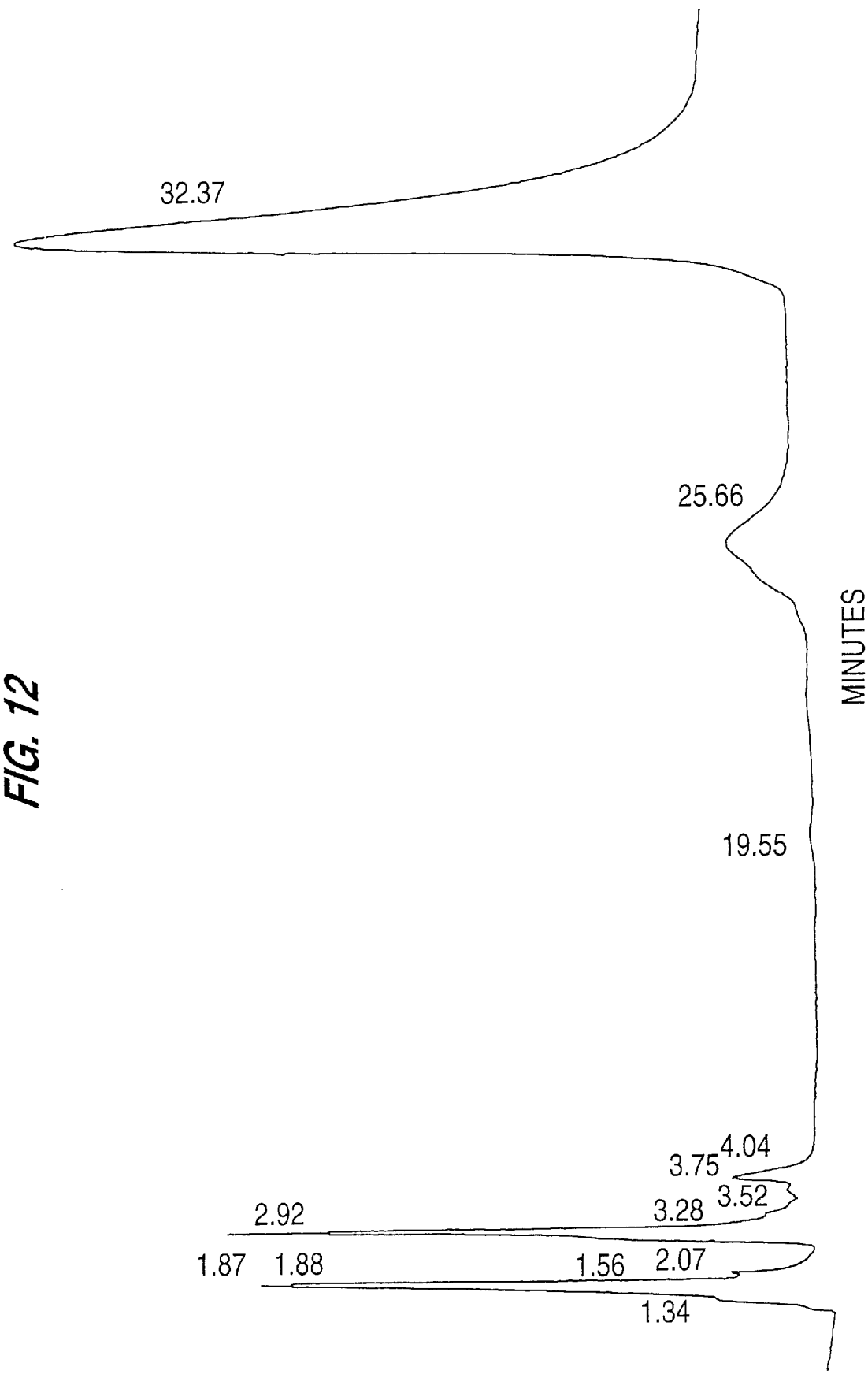
FIG. 12 represents a HPLC profile of the extract of the present invention.

For HPLC, a Bondapak C18 reverse phase column (Waters) was used, and the mobile phase was 95% MeOH/95% $H_2O$ (6:4, v/v). Flow rate was 1.2 ml/min. Peaks were detected by UV detection at 263 nm. New peaks were detected in the extract of the present invention at RT (retention time) 25.66 and 32.37 min. FIG. 10 shows the HPLC profile of the extract from *Ricinus communis* L. and FIG. 11 shows the profile of the extract from *Coptis chinensis*. FIG. 12 shows the HPLC profile of the extract of the present invention. From the results of UV scanning and HPLC, we proposed that new materials were made from the each components of the extract. The new substances are of low molecular weight and slightly hydrophobic materials.

EXAMPLE 5

Characterization of the Extract by Differential Solvent Extraction

Figure 13:
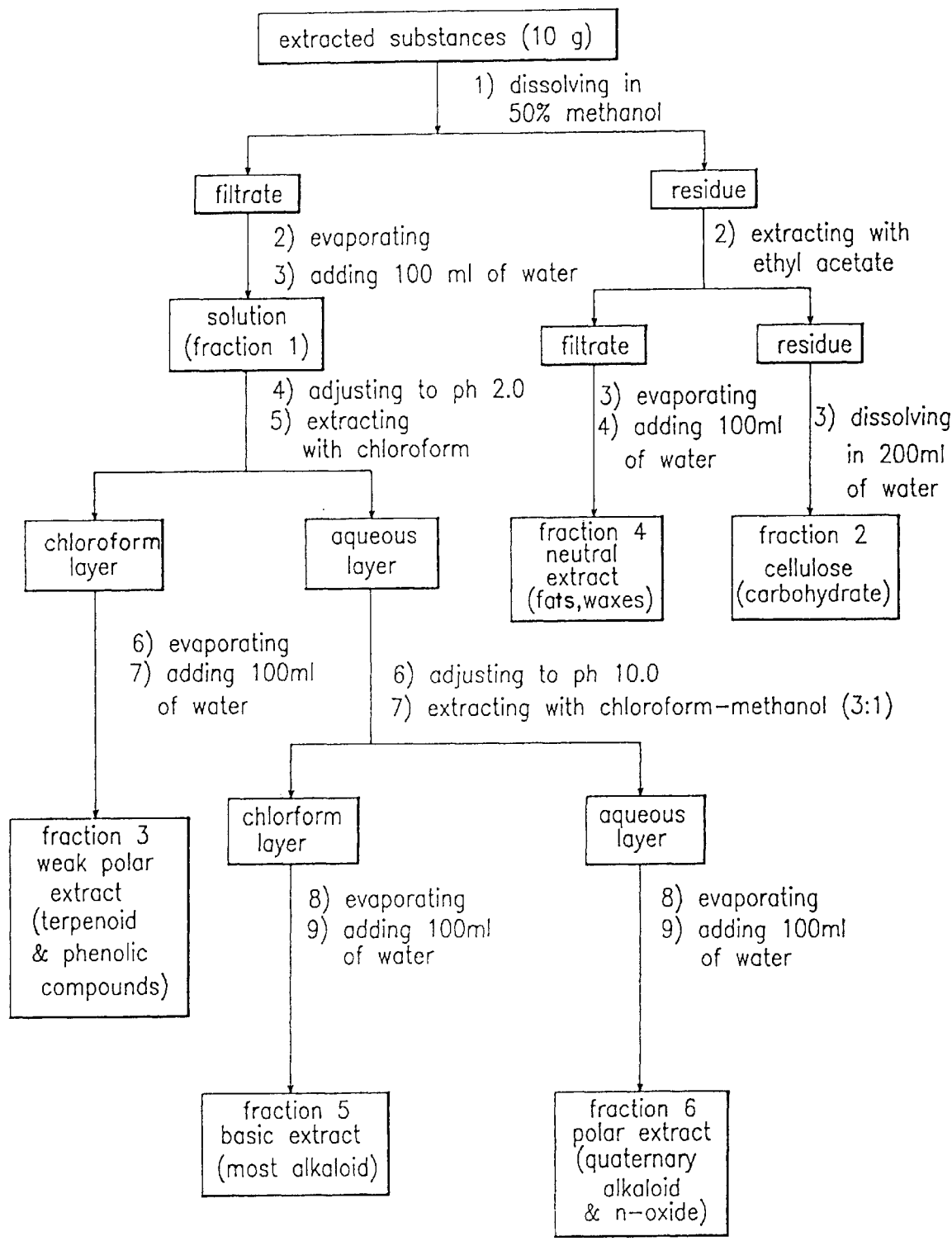
FIG. 13 is a diagram showing a process for obtaining a product of the present invention by fractionating according to solvent polarity.

The extract of the present invention was separated into five different fractions in accordance with a method shown in FIG. 13 and then subjected to thin layer chromatography (TLC). Each fraction was dissolved in distilled water at a concentration of 100 g of the extracted substance per 1 L of water except that the Fraction 2 (found to have lower solubility in water), was dissolved at 50 g/L. For comparative purposes, the same procedure was independently repeated with berberine (obtained from Sigma Chemical Co., St. Louis, Mo., U.S.A.) which is a main quaternary alkaloid of Coptis sp.

Ten g of the extract prepared according to Example 1 was dissolved in 100 mL of a 1:1 mixed solvent of water and methanol and filtered. The filtrate was evaporated to remove methanol and dissolved in 100 mL of distilled water. The solution thus obtained was defined as Fraction 1. The Fraction 1 was adjusted to pH 2.0 and then agitated with chloroform. The emulsion was allowed to separate into a chloroform layer and an aqueous layer. The chloroform layer was dried thoroughly and the resulting residue was dissolved in 100 mL of distilled water. The solution thus obtained was defined as a Fraction 3. The aqueous layer from the chloroform extraction was adjusted to pH 10.0 and then agitated with a mixed solution of chloroform and methanol (3:1) and the emulsion was allowed to separate into a chloroform layer and a methanol:water layer. The chloroform layer was dried and then the residue was dissolved in 100 mL of distilled water to give Fraction 5. The methanol:water layer was dried and then the residue was dissolved in 100 mL of distilled water to give a Fraction 6.

In addition, the retentate of the above-described filtration was extracted with ethyl acetate. The solvent was removed by evaporation and the resulting residue was dissolved in 100 mL of distilled water to give Fraction 4. The material not soluble in ethyl acetate was dissolved in 100 mL of distilled water to give Fraction 2.

Each fraction was spotted on a thin layer chromatographic (TLC) sheet of silica gel in a conventional manner using a mixed solvent of butanol, acetic acid and water (4:1:1) as a developing solvent and an UV lamp for detection of the components of the samples. After spotting, the samples were dried under a nitrogen stream. A filter paper was placed in the TLC chamber, and the same solvent was poured into the chamber before running. Vacuum grease was used to seal the chamber covered with a cover glass.

Figure 14:
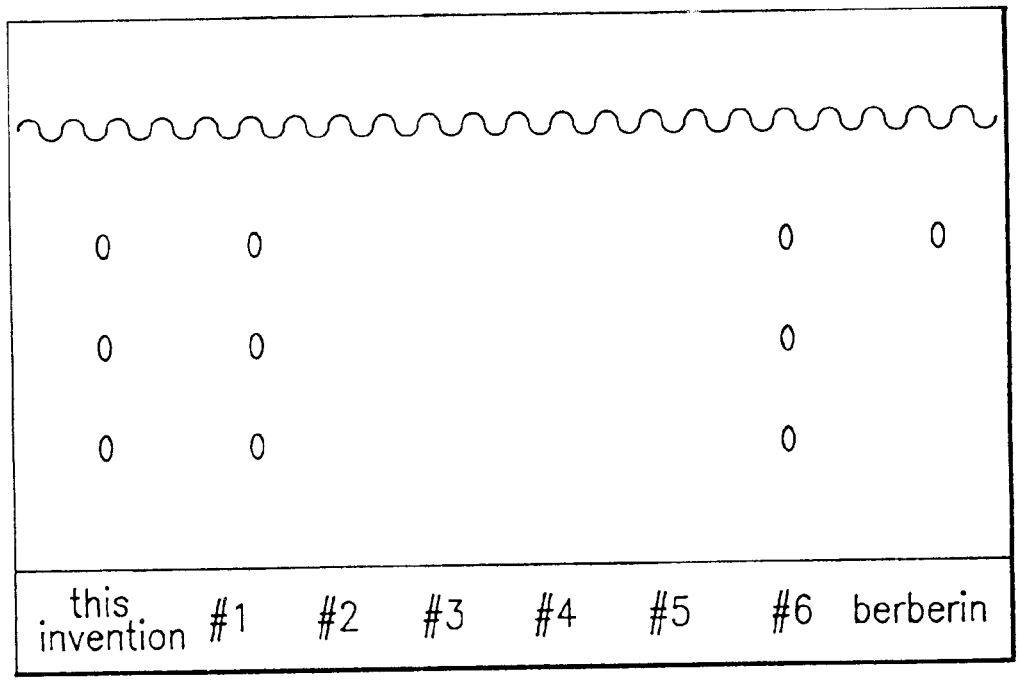
FIG. 14 represents a thin layer chromatogram for a fraction produced by the process shown in FIG. 6 and berberine.

The results of the thin-layer chromatography are shown in FIG. 14. Referring to FIG. 14, Fractions 1 and 6 have the same TLC pattern as an unfractionated sample of the extracted substances of the invention. From this result, it is confirmed that the extracted substances of the invention mainly consist of polar substances such as a quaternary alkaloid of the Fraction 6 and N-oxide, and have an Rf value the same as berberine.

EXAMPLE 6

Separation of Fraction 6 by Ion Exchange Chromotography

This example illustrates a separation of various components of the extract of the present invention by means of ion exchange resins. The Fraction 6 of the Example 3 was separated into Fractions 6-S and 6-Q using Mono Q and Mono S ion exchange cartridges.

Figure 15:
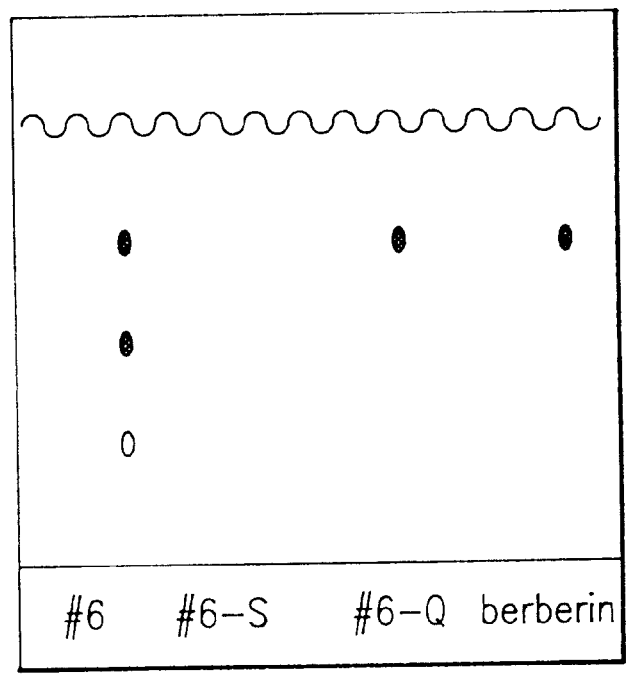
FIG. 15 represents a thin layer chromatogram for fractions produced by the process shown in FIG. 16 and further fractionated by an ion exchange resin.

The Mono Q and Mono S cartridges were washed with methanol and saturated with distilled water. 1.0 mL of Fraction 6 was loaded on each column and eluted using a mixed solvent of butanol, acetic acid and water (4:1:1). The eluting compounds were analysed by TLC, and their chromatograms were also compared with Fraction 6 and berberine. Each eluate was subjected to thin layer chromatography (TLC). Independently, the same procedure was repeated with berberine for comparison. The results are shown in FIG. 15. Rf value of Fraction 6-Q is the same as that of berberine. Therefore Fraction 6-Q is considered to be berberine. No substance was detected in the eluate of the Mono-S cartridge.

EXAMPLE 7

Separation of Fraction 6 by HPLC

This example illustrates a separation of components of the extract of the present invention by high performance liquid chromatography (HPLC). The Fraction 6 of the Example 3 was separated into Fractions 6-1, 6-2, 6-3, 6-4, 6-5 and 6-6. Fraction 6 was analyzed by high performance liquid chromatography (HPLC). A $\mu$-Bondapak $C_{18}$ column was used in the HPLC. Each fraction was detected at 254 nm by UV detection. Mobile phase was phosphate buffer in acetonitrile. Flow rate was 1.0 ml/min. Each fraction was collected according to the retention time (RT):

Fraction 6-1; RT 0–13 min.

Fraction 6-2; RT 13–16 min.

Fraction 6-3; RT 16–21 min.

Fraction 6-4; RT 21–26 min.

Fraction 6-5; RT 26–31 min.

Fraction 6-6; RT 31–38 min.

Figure 16:
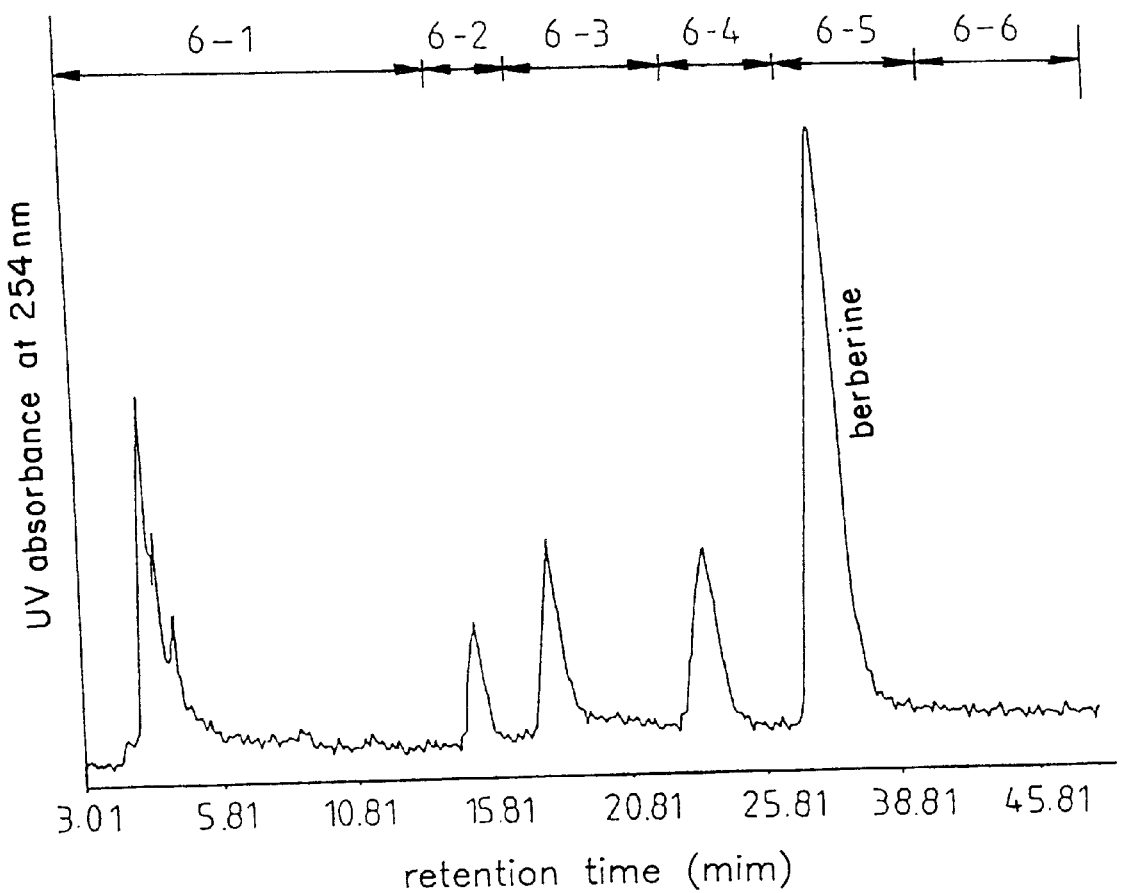
FIG. 16 represents a high performance liquid chromatogram for Fraction 6.
Figure 17:
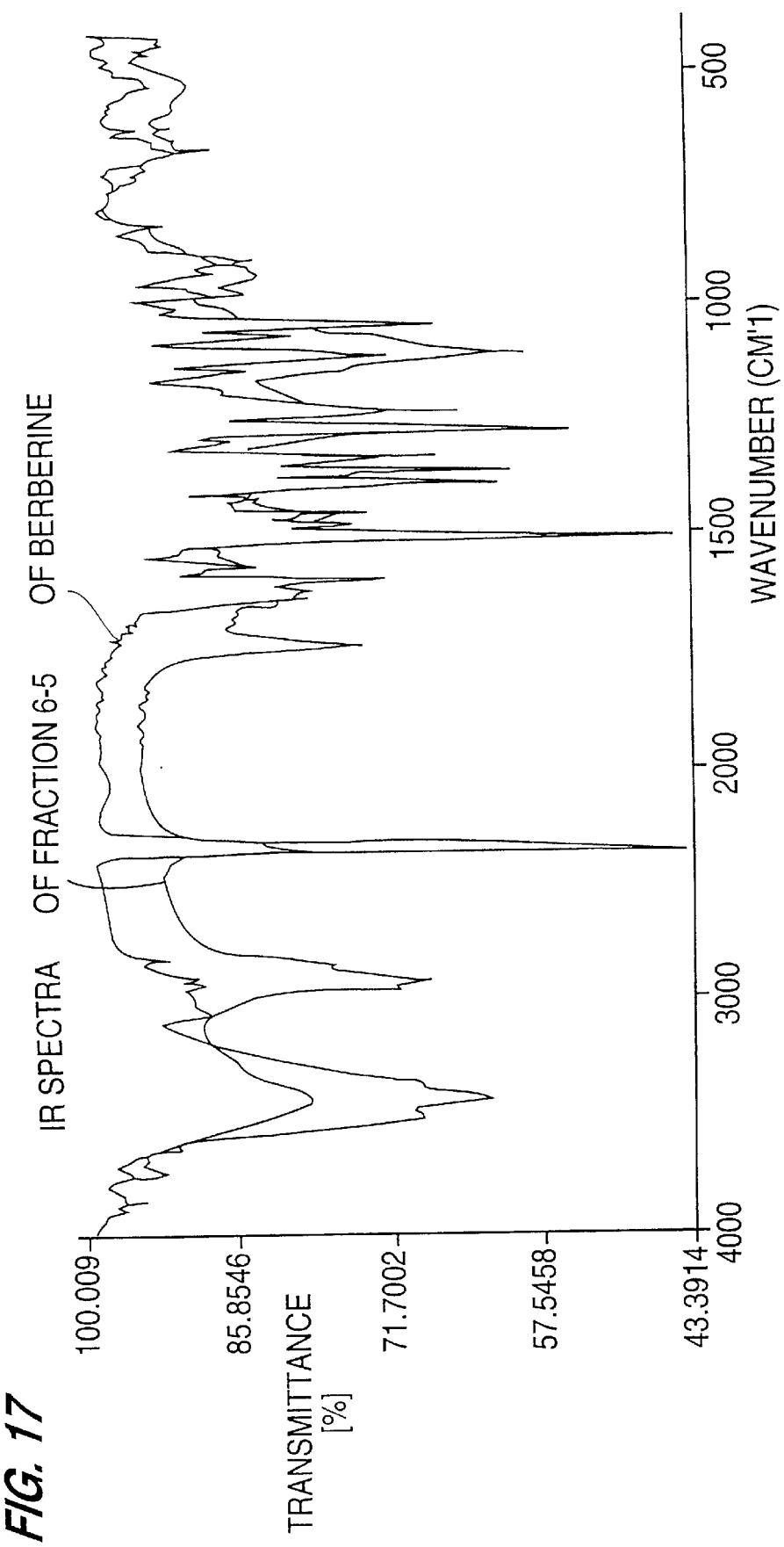
FIG. 17 represents infrared (IR) spectra for Fraction 6-5 and berberine.

The organic solvent in each fraction was removed using a rotatory evaporator and the residue was dissolved in 50 mL of distilled water. The entire 50 mL sample was loaded onto a Sep-Pak C18 cartridge (Waters). The column was then washed with sufficient water to remove phosphate salt of the mobile phase. After the phosphate is removed, as discerned by disappearance of any salty taste from the column eluate, the adsorbed materials were eluted. Flow rate was 1.0 ml/min. Mobile phase was phosphate buffer in acetonitrile (9:1, v/v). Peaks were detected by UW detection at 254 nm. The resulting HPLC profile is shown in FIG. 14. Referring to FIG. 16, the Fraction 6-5 has the same retention time as berberine.

EXAMPLE 8

Spectroscopic Analysis of Fraction 6-5

The Fraction 6-5 was analyzed to identify its chemical structure. To this end, infrared spectroscopy (IR: IFS 66/Bruker), $^1$H nuclear magnetic resonance spectroscopy ($^1$H-NMR: AQMS-500/Bruker), $^{13}$C nuclear magnetic resonance spectroscopy ($^{13}$C-NMR: AMX-500/Bruker) and mass spectrometry (HP5988A Quadropole Mass Spectrometer) were employed. Independently, the same procedures were repeated with berberine for comparison. The results are shown in FIGS. 17 to 22.

Figure 18:
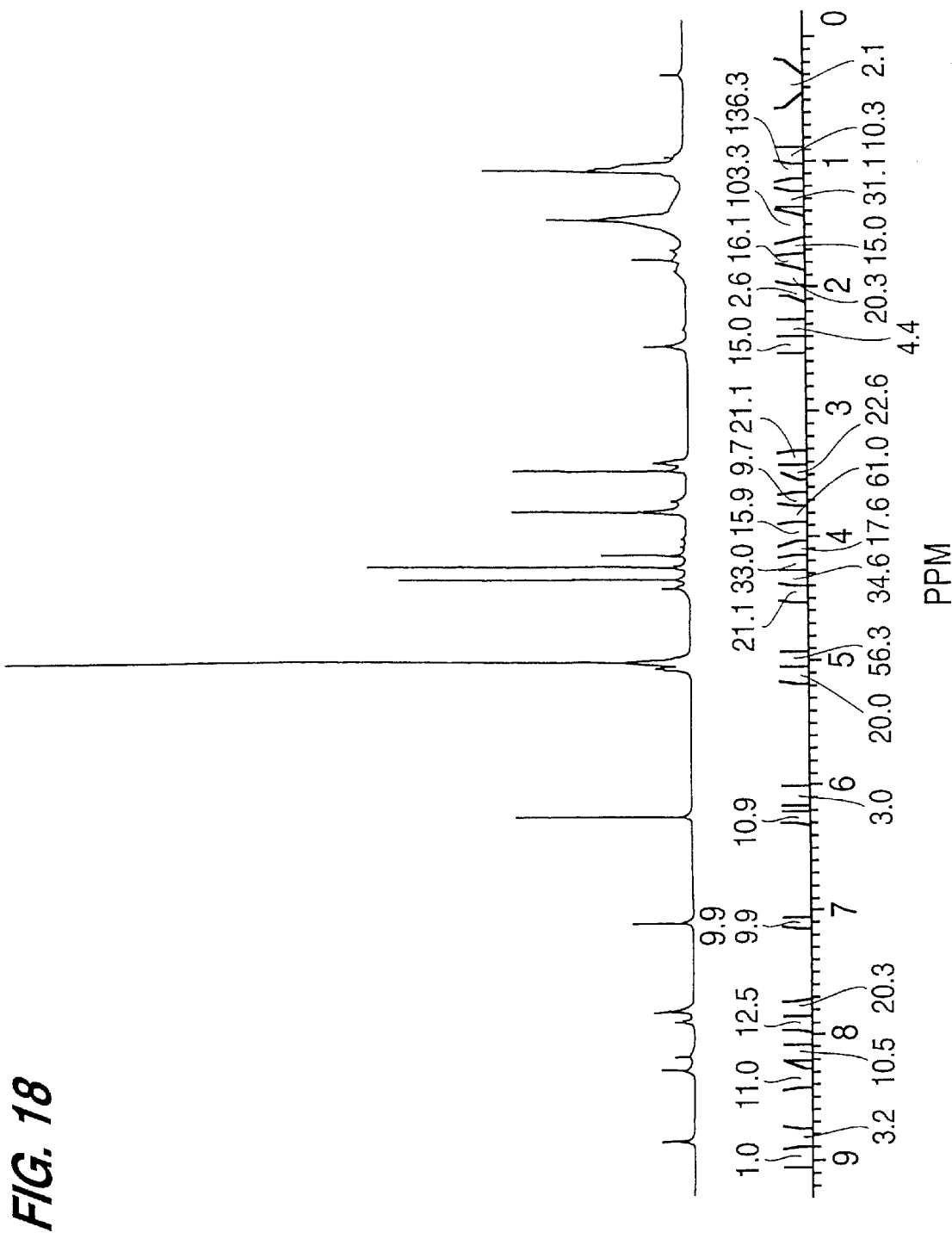
FIG. 18 represents a $^1$H-NMR spectrum for Fraction 6-5.
Figure 19:
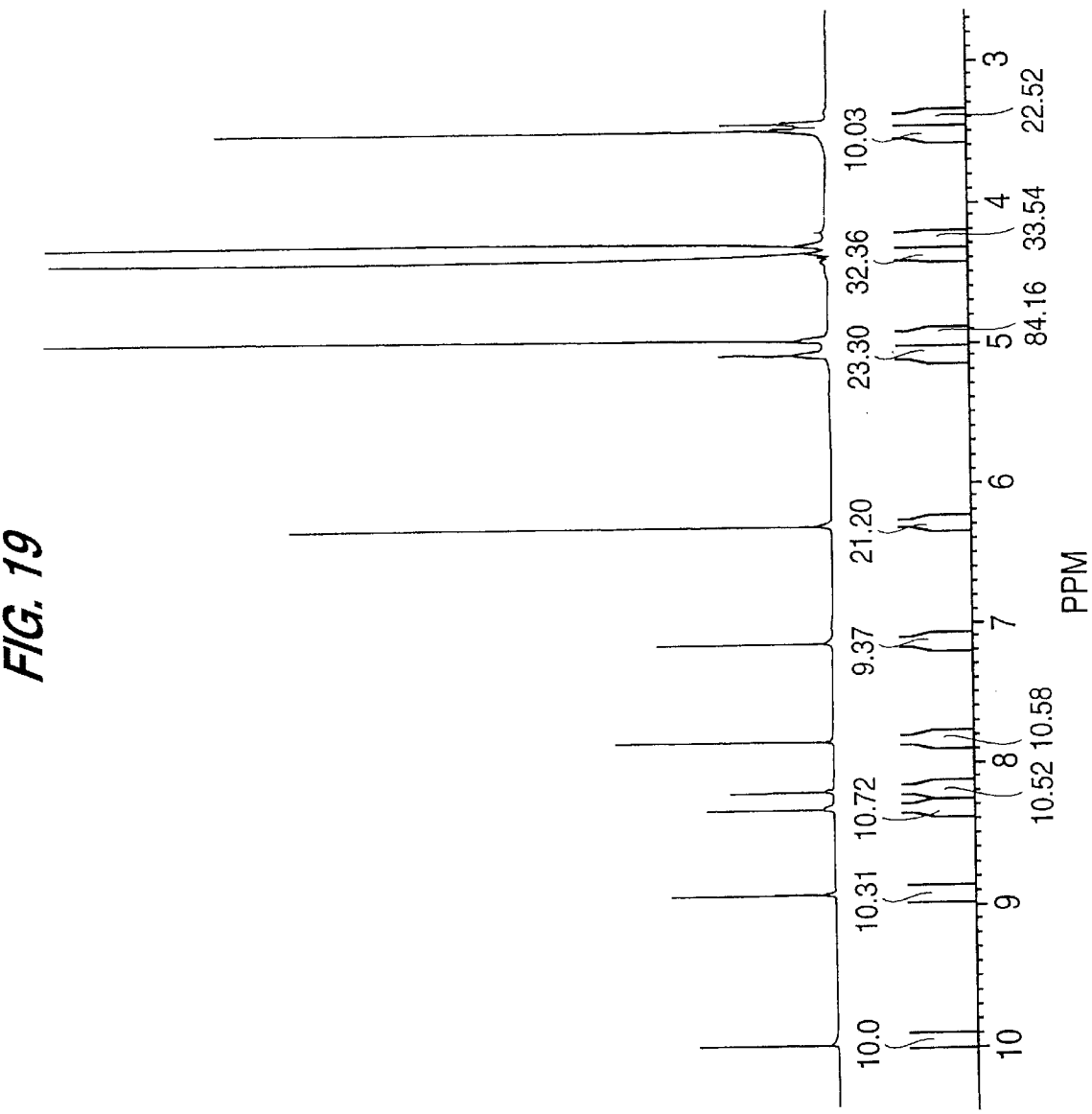
FIG. 19 represents a $^1$H-NMR spectrum for berberine.
Figure 20:
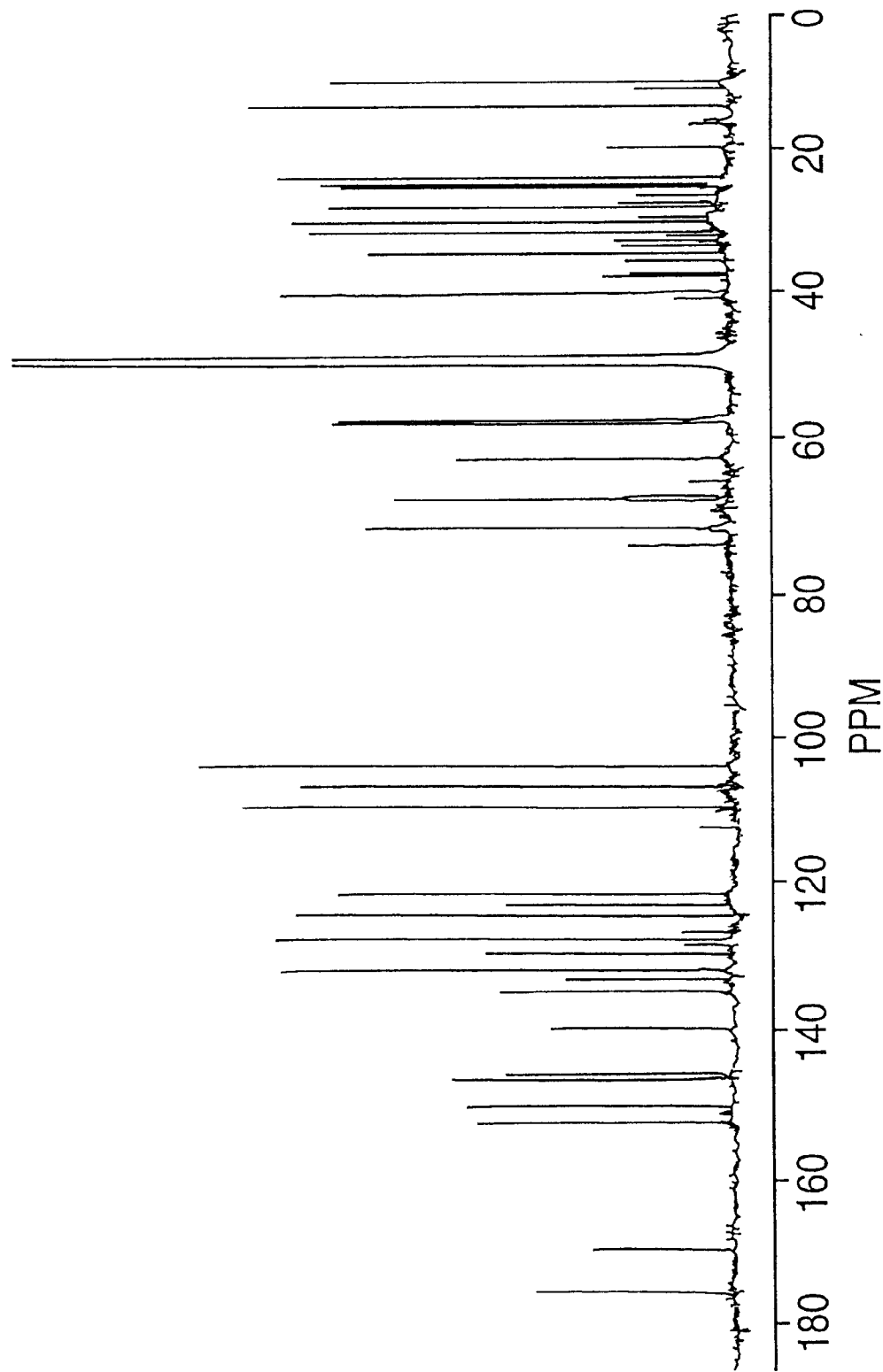
FIG. 20 represents a $^{13}$C-NMR spectrum for Fraction 6-5.
Figure 21:
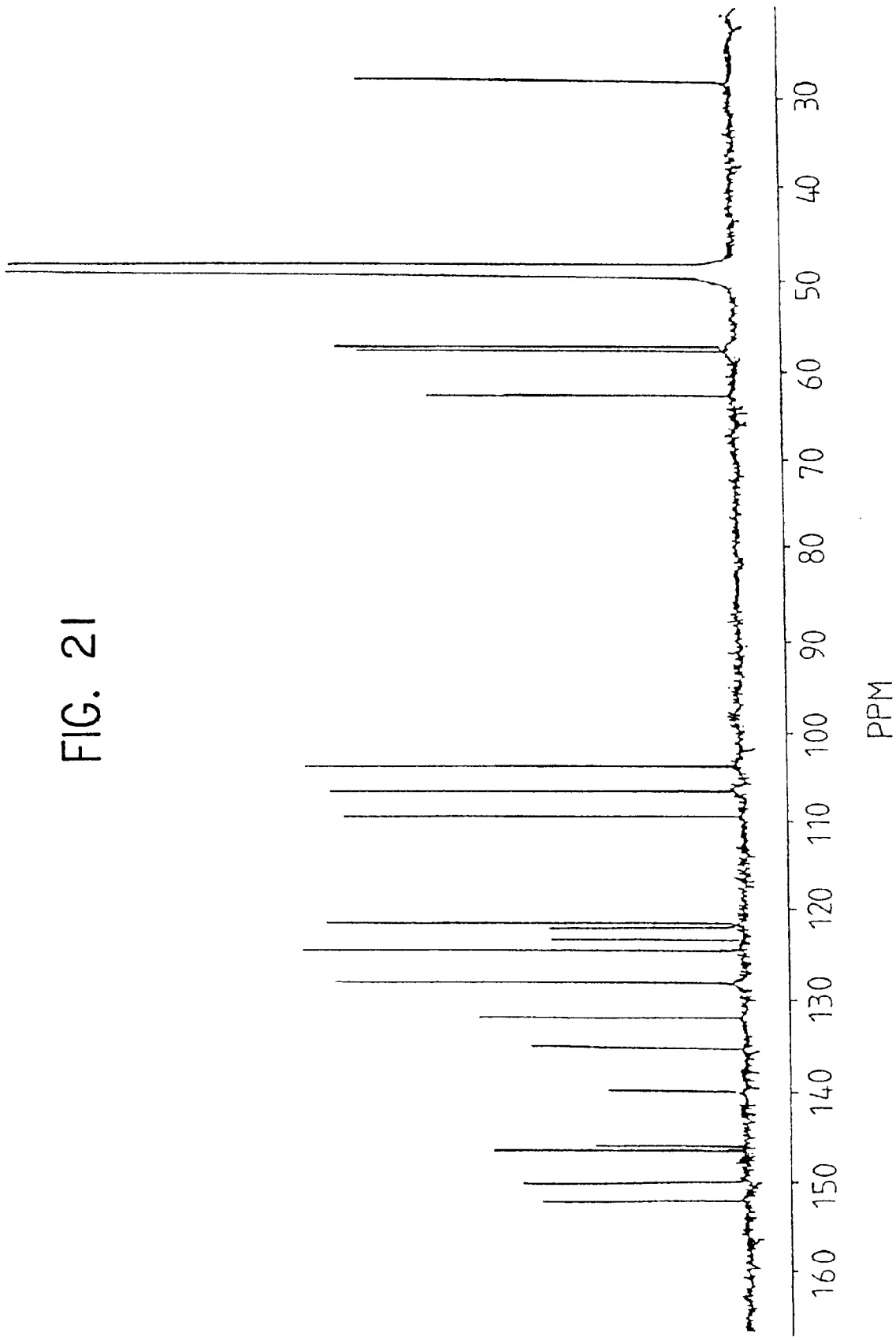
FIG. 21 represents a $^{13}$C-NMR spectrum for berberine.
Figure 22A:
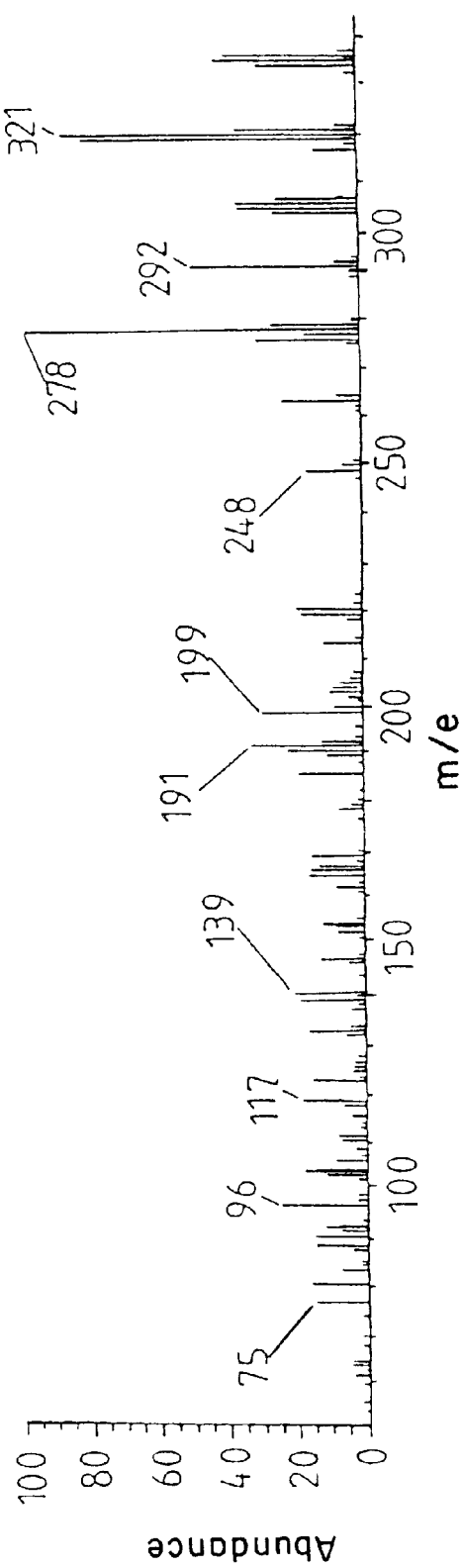
FIGS. 22a–b represent mass spectra for Fraction 6-5 (22a) and berberine (22b).
Figure 22B:
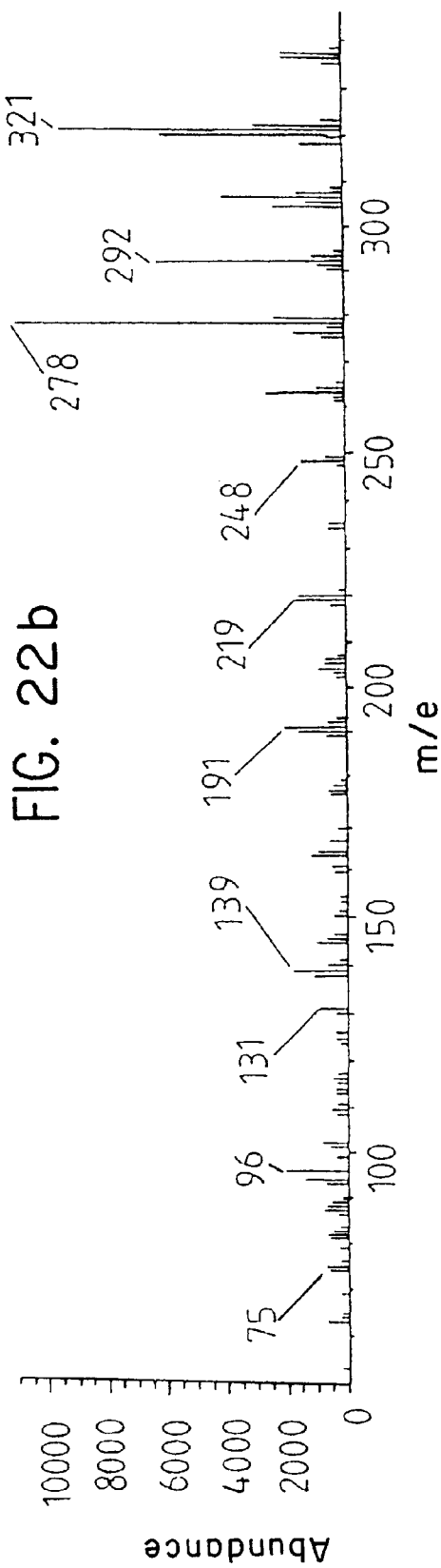

Referring to FIGS. 17 to 22, FIG. 17 represents IR spectra for Fraction 6-5 (a) and berberine (b); FIG. 18 represents a $^1$H-NMR spectrum for Fraction 6-5; FIG. 19 represents a $^1$H-NMR spectrum for berberine; FIG. 20 represents a $^{13}$C-NMR spectrum for Fraction 6-5; FIG. 21 represents a $^{13}$C-NMR spectrum for berberine; and FIG. 22 represents mass spectra for Fraction 6-5 (a) and berberine (b).

From these results, it is concluded that the Fraction 6-5 comprises berberine even though it has a minor amount of impurities.

EXAMPLE 9

Anti-Oxidation Effect of the Extract

It is known that substances such as flavonoids, which have strong anti-oxidative activity, also have activity as inhibitors of HIV replication. It was reported that flavonoids exhibited potencies against HIV-1 and HIV-2 reverse transcriptase ((1) Tan, G. T., Miller, J. F., Kinghorn, A. D., Hughes, S. H. and Pezzuto, J. M.; HIV-1 and HIV-2 reverse transcriptases: a comparative study of sensitivity to inhibition by selected natural products. Biochem. Biophys. Res. Commun. 185(1) :370–378, 1992. (2) Vlietinck, A. J., Vanden, B. D. A.; Can ethnopharmacology contribute to the development of antiviral drugs? J. Ethnopharmacol. 32(1–3): 141–153, 1991.)

The mode of inhibition of flavonoids (baicalein, quercetin, quercetagetin, myricetin) was partially competitive (HIV reverse transcriptase) with respect to the template-primer complex, (rA)n, (dT), and noncompetitive with respect to the triphosphate substrate, dTTP ((1) Ono, K., Nakane, H., Fukushima, M., Chermann, J. C., Barre, S. F.; Differential inhibitory effects of various flavonoids on the activities of reverse transcriptase and cellular DNA and RNA polymerase. Eur. J. Biochem. 190(3): 469–176, 1990. (2) Ono, K., Nakane, H.; Mechanisms of inhibition of various cellular DNA and RNA polymerases by several flavonoids. J. Biochem. Tokyo, 108(4):609–613, 1990.)

It has been previously shown that *Ricinus communis* L. contains $C_6$-$C_3$-$C_6$ compounds such as flavonoids and the like which have strong antioxidant properties. $C_6$ moiety of flavonoids is a benzene ring. Flavonoid compounds usually occur in plants as glycosides in which one or more of the phenolic hydroxyl groups are combined with sugar residues.

Kang et al. (Kang, S. S., Cordell, G. A., Sqejarto, D. D., and Fong, H. H. S., Alkaloids and flavonoids from *Ricinus conmmunis* L. J. Natural Products 48(1): 155–157, 1985) reported that *Ricinus communis* L. contained many kinds of flavonoids such as kaempferol-3-O-β-D-xylopyranoside, kaempferol-3-O-β-D-glucopyranoside, kaempferol-3-O-β-rutinoside, quercetin-3-O-β-D-glucopyranoside, quercetin-3-O-β-D-xylopyranoside, and quercetin-3-O-β-rutinoside.

Therefore, we characterized the extract of the present invention with respect to its ability to function as an antioxidant. We compared the extract to the known antioxidant t-butylhydroxy toluene (BHT) using a chemiluminescence assay developed in this laboratory. (Hong, E. K., Kim, Y. K., Lee, W. C., Shin, H. K., and Kim, J. B.; Measurement of antioxidation activity based on chemiluminescence reaction. In: Bioluminescence and Chemiluminescence (Status Report), Eds. Szalay, A. A., Kricka, L. J., and Stanley, P., John Wiley & Sons Ltd. London, England, pp. 244–246, 1993.) The experiments show that the extract of the present invention has superior antioxidant activity. These results show that the extract of the present invention contains potent antioxidants. Therefore, it is proposed that the extract has anti-HIV effect.

Materials: microperoxidase (MP, Sigma Chemical Company, St. Louis, Mo., U.S.A.), aminobuty ethylisoluminol (ABEI, Sigma Chemical Company, St. Louis, Mo., U.S.A.), t-butylhydroxy toluene (BHT, Sigma Chemical Company, St. Louis, Mo., U.S.A.).

An ABEI-microperoxidase-$H_2O_2$ system was used to assay the antioxidant activity of the extract of the present invention and also that of the known antioxidant BHT. The activity of berberine as an antioxidant was also assessed.

ABEI was used at 0.18 $\mu$M. Compounds being assayed were used at 10 mg/ml as a maximum concentration and also at serial dilutions. 200 $\mu$L of ABEI, t-butylhydroxy toluene (BHT), pure berberine or the extracted substance at 10 mg/ml (or a serial dilution thereof) were put in a polystyrene tube suitable for use in a Berthold 9502 luminometer. Hydrogen peroxide (0.35%) and microperoxidase (0.01 mg/ml) were autoinjected into the tube to start the chemiluminescence reaction. Chemiluminescence from the reaction was measured for 2 seconds using a Berthold Luminometer 9502 (Clilumat). In control samples distilled water and ethyl alcohol were used. The antioxidant activity of the extract was compared with commercial antioxidant BHT. The antioxidant activity of BHT has been studied for many years (Branen, A. L.; Toxicological and biochemistry of butylated hydrosyanisole and butylated hydroxytoluene. J. Am. Oil Chem. Soc. 52:59, 1975). BHT removes free radicals in oxidation reactions, and it inhibits oxidation of materials.

An antioxidant present in the sample will prevent ABEI from being oxidized by microperoxidase, thus inhibiting chemiluminescence. Antioxidant activity was calculated from the chemiluminescence intensity using the following expression:

$$\text{Inhibition of chemiluminescence intensity} = 100 - \frac{\text{the light intesity of experimental group}}{\text{the light intensity of control group}} \times 100\%$$

TABLE 4

Percentage of inhibition of light intensity

| Conc. of Drug mg/ml | BHT | Extract of the invention | Berberine |
|---|---|---|---|
| 0.63 | 93 | 38 | 11 |
| 1.25 | 97 | 96 | 12 |
| 2.5 | 98 | 99 | 12 |
| 5.0 | 99 | 99.2 | 21 |
| 10.0 | 99.8 | 99.8 | 57 |

The above results show that berberine, though shown above to be a component of the extract of the present invention, has a much lower antioxidant activity than the total extract. Thus, the extract of the present invention is distinguishable from pure berberine. Furthermore, we anticipate that the antioxidants present in the extract increase the anti-HIV effect of such berberine as is present in the extract.

EXAMPLE 10

Compositional Analysis of the Extract

The composition of the extract prepared as in Example 1 is shown in Table 5.

TABLE 5

The composition of the extract

| Component | Content (%) |
|---|---|
| Protein | 30 |
| Reducing Sugar | 18–20 |
| Crude Ash | 10–11 |
| Alkaloids | |
| Berberine | 8–10 |
| Protoberberine | 5–6 |
| Amine | Trace |
| Amino Acids | 5–6 |
| Organic acids other than amino acids (35 Kinds) | 4–5 |
| Alcohols | 3–4 |

1) Crude protein

The content of crude protein was investigated using the Kjeldahl Nitrogen Analysis Method. The content of Crude protein in the extracted substance was about 30% as determined by this method. The method is briefly described below:

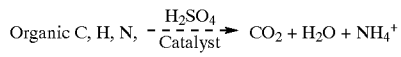

Organic compounds containing nitrogen were degraded in boiling $H_2SO_4$, producing ammonium ion as a product. The amount of the resultant ammonium ion is quantitated by titration with acid, and the content of nitrogen can be calculated.

Figure 24:
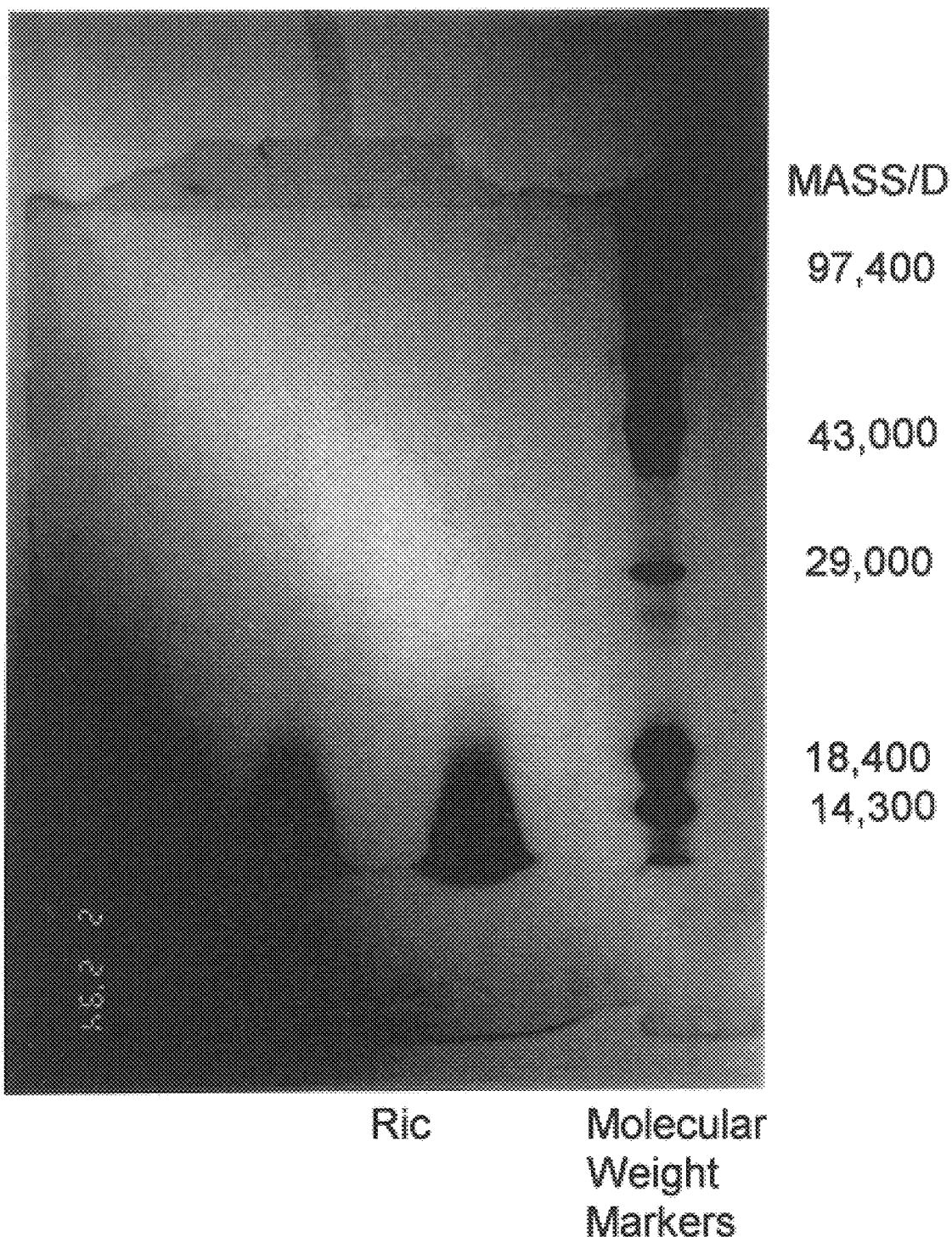
FIG. 24 represents the result of electrophoresis of the protein extracted by the method shown in FIG. 23.

We consider that the majority of the nitrogen is derived from protein. It was known that seeds of *Ricinus communis* L. contained a toxic protein, ricin. Proteins in the extract of the present invention were isolated by salt precipitation using ammonium sulfate solution (70%), and lyophylized as following (FIG. 23). The isolated protein fraction was analyzed by electrophoresis in 12% polyacryamide gel in the presence of 0.1% sodium dodecyl sulfate (FIG. 24). According to the result of electrophoresis, monomer (MW 33,000, consistent with ricin monomer) or dimer (MW 66,000, consistent with ricin dimer) of ricin was not detected. However, a large amount of low molecular weight (below 10,000) peptide was detected.

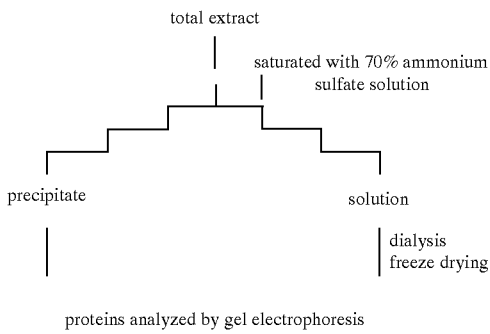

Protocol for isolation of proteins from the extract 2) reducing sugar

The amount of reducing sugar in an extract prepared as in Example 1 was analyzed by the Shaeffer-Somogyi method. The extract was treated with copper sulfate and potassium iodide-potassium oxalate solution, and then titrated with sodium thiosulfonate.

The amount of reducing sugar measured by this method is about 18–20%. Since the amount of nonreducing sugar was not measaured, the extract possibly contains additional carbohydrates. The above table shows that those substances for which the extract has been characterized comprise a total of 83 to 92% of the dry weight of the extract. Thus, carbohydrates consisting of non-reducing sugars perhaps constitute as much as 8 to 17% of the extract.

3) crude mineral

A sample of the extract was burned at 500–550° C. Ash, representing the crude mineral fraction, in the amount of 10 to 11% of the weight of the sample, remained unvolatilized.

4) Amino Acid Analysis

Figure 25:
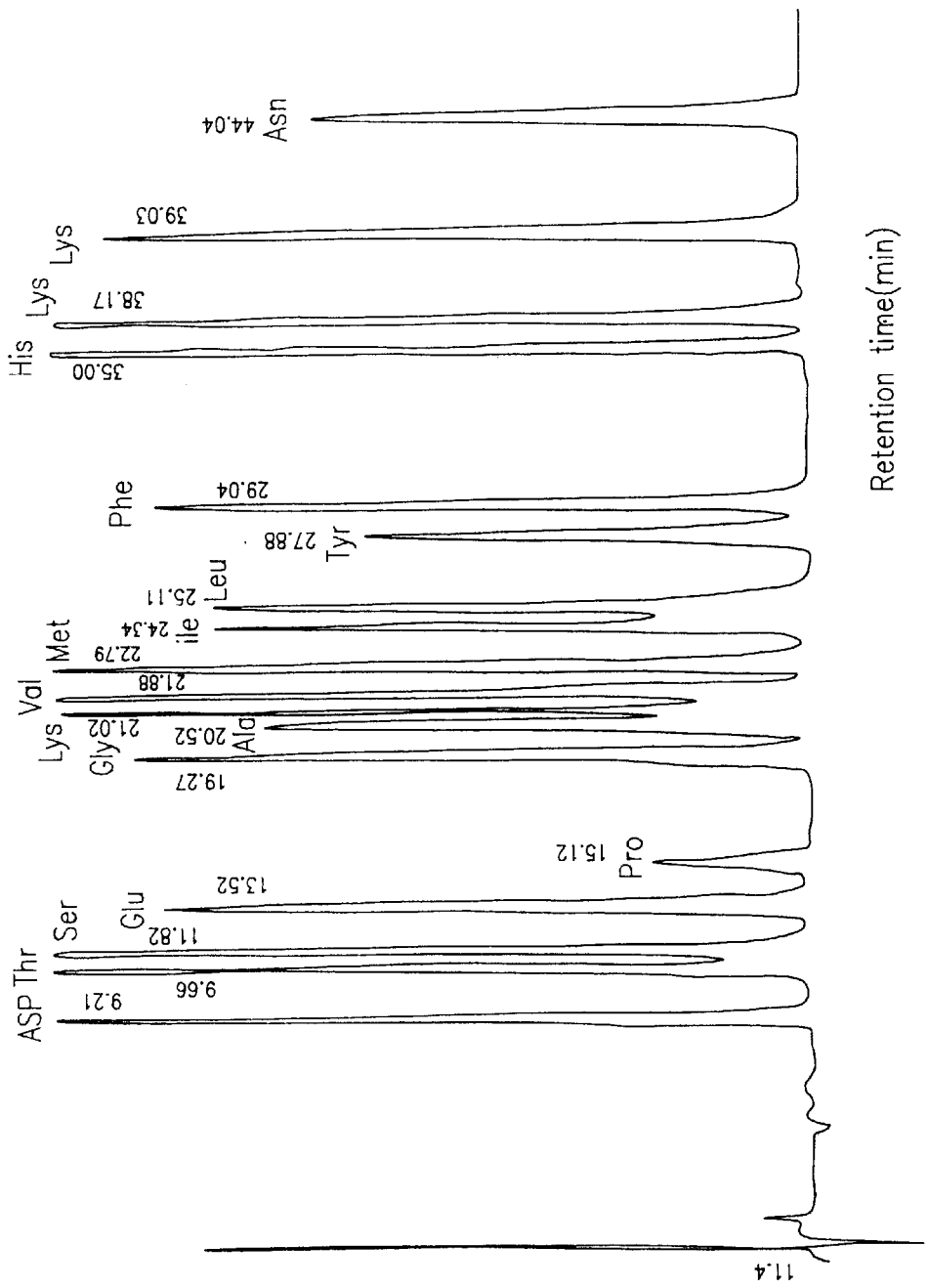
FIG. 25 represents a chromatographic analysis of amino acid standards.
Figure 26:
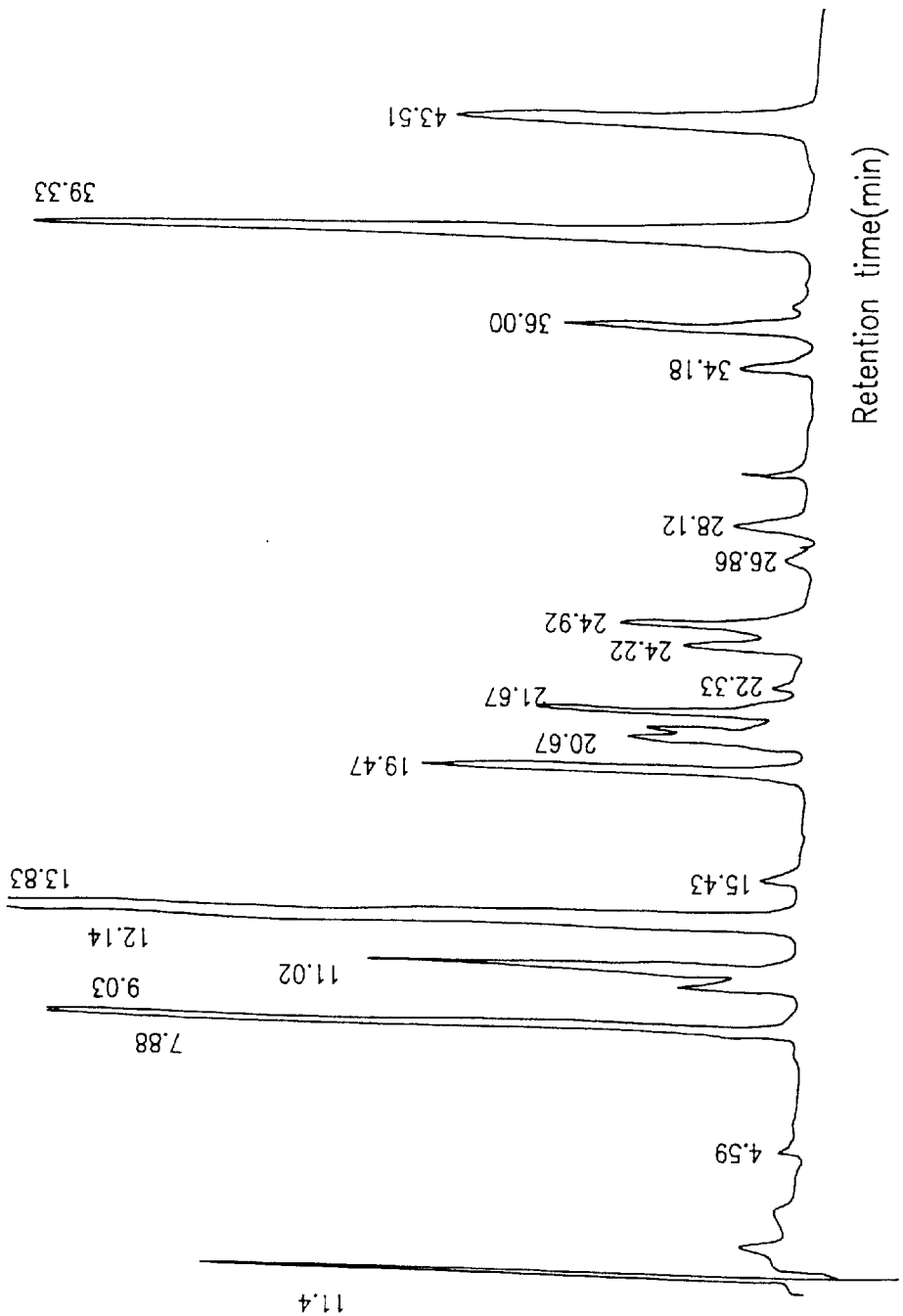
FIG. 26 represents a chromatographic analysis of the amino acids of the protein component of the extract of the invention.

The amino acid composition of the crude protein fraction was investigated using an amino acid analyzer and gas chromatography. FIG. 25 shows amino acid analysis chromatogram of standard amino acids using a Pharmacia LKB Alpha Plus amino acid analyser. FIG. 26 shows an amino acid analysis chromatogram of the extract of the present invention. Glutamic acid and aspartic acid were the predominant amino acids identified.

Figure 27:
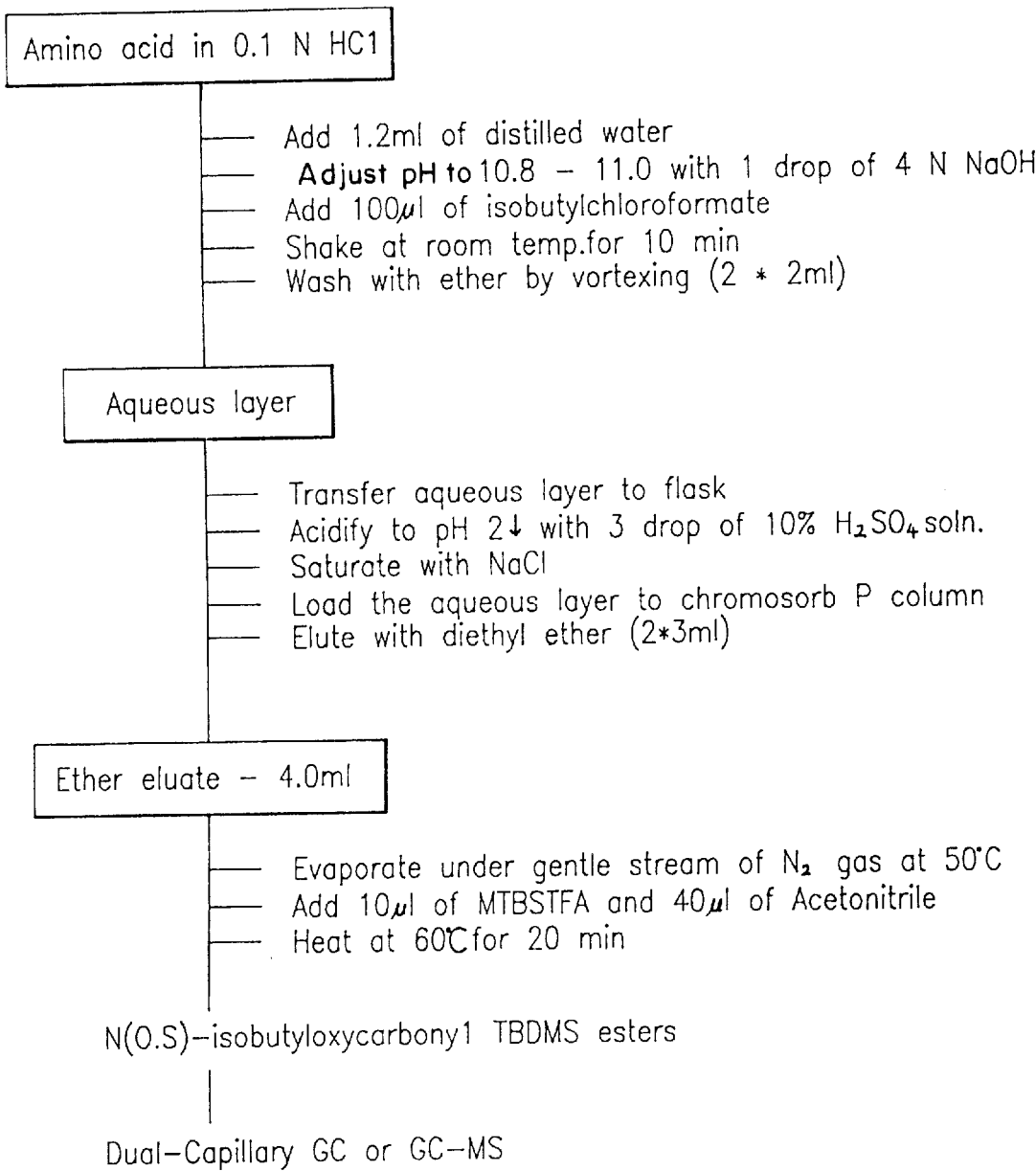
FIG. 27 represents a flow chart for TBDMS derivatization of amino acid standards.
Figure 28:
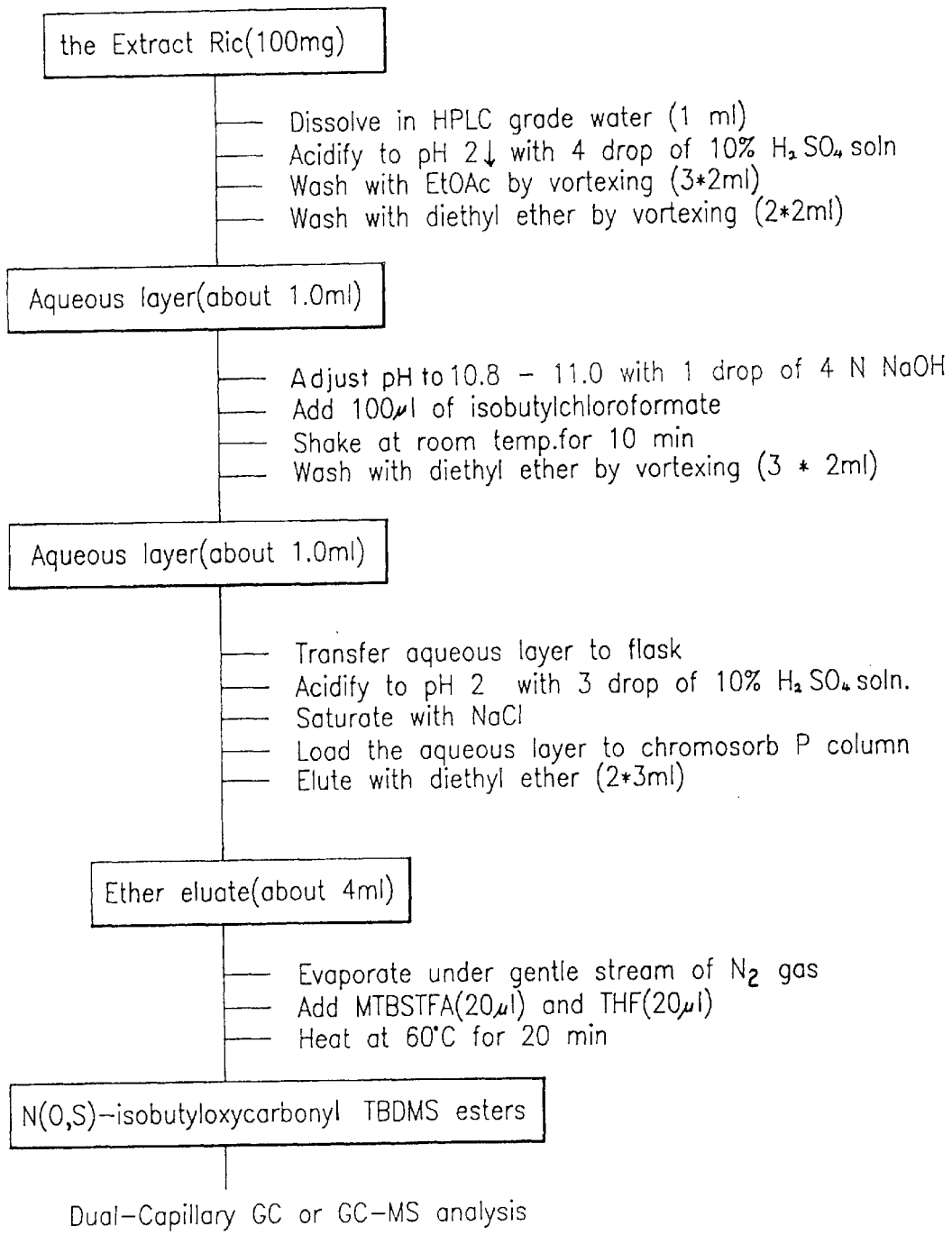
FIG. 28 represents a flow chart for TBDMS derivatization for amino acids of the protein component of the extract of the invention.
Figure 29:
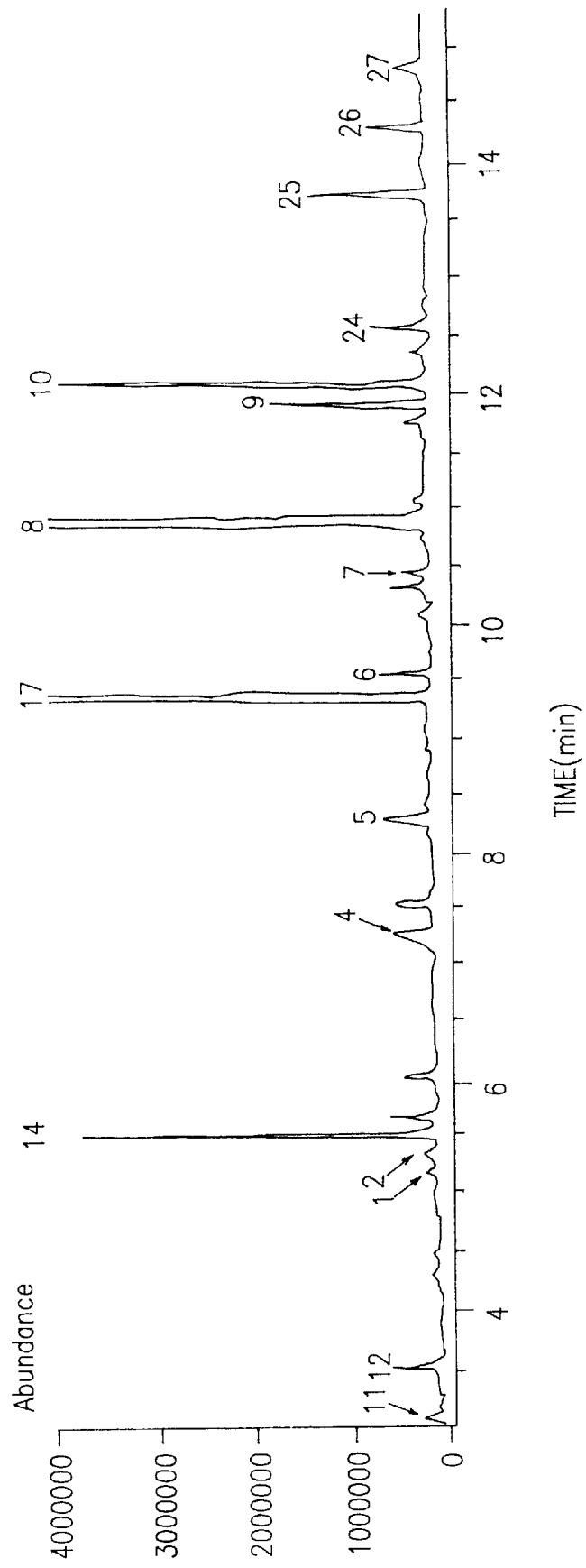
FIG. 29 represents amino acid profiles of the extract as the N(O,S)-isoBOC TBDMS derivatives.

Amino Acid Analysis by Gas Chromatography:

The content of amino acids was investigated using gas chromatography, as shown in FIGS. 27–31. Amino acids were extracted by N(O,S)-isobutyloxycarbonyl (isoBoc) derivatization method. The functional group containing carboxyl residue was derivatised by tertbutyldimethylsilyl (TBDMS) derivatization method (FIGS. 27, 28). Amino acids were analysed by DB-5 and DB-17 dual-capillary column GC system, and temperature-programmed retention index (RI) of each compound was obtained (FIG. 29). Each compound was identified from RI and mass spectra through screening library in the GC chemstation. The amounts of apartic acid, asparagine and glutamic acid are higher than other amino acids as shown in Table 6. Alanine, glycine, and serine were also detected.

Gas Chromotography for amino acid analysis:
GC model: GC 5890A gas chromatograph (Hewlett-Packard, Avondale, U.S.A.)
HP-5890A GC Workstation
   flame ionization detector (FID)
   split/splitless injection port
   on-column injection port
HP-5970B MSD
   (HP-5890A series II gas chromatograph with HP-59940A MS Chemstation)
Operating conditions for GC analysis:
Column: Dual-Capillary Column system (J & W Scientific, Rancho, U.S.A.)
   DB-5 and DB-17 fused silica capillary columns
   30 m×0.25 mm I.D., 0.25 μm df)
Column temp.: 150° C. (2 min.) to 280° C. at 3° C./min.
Injection mode: Split injection mode at 280° C.
Detector: flame ionization detector (FID) at 300° C.
Operating conditions for GC-MS analysis:
Column: HP-1 cross-linked capillary column
   (12 m×0.20 mm I.D., 0.33 μm df)
HP-5 cross-linked capillary column
   (25 m×0.20 mm I.D., 0.33 μm df)
Column temp.: 150° C. (2 min.) to 280° C. at 10° μC./min
Injection mode: Split injection mode at 280° C.
Detector: flame ionization detector (FID) at 300° C.

TABLE 6

Amino acids found in the extract by tbdms. 1 MS library searching

| No. | Compound | Library match quality[%] | Normalized area (%) the extract |
|---|---|---|---|
| 1 | β-Alanine | 83 | trace |
| 2 | Glycine | 91 | 1.19 |
| 3 | Proline | 76 | n.d.[a] |
| 4 | γ-Aminobutyric | 93 | trace |
| 5 | Pyroglutamic acid | 90 | 2.64 |
| 6 | Serine | 90 | 3.25 |
| 7 | Homoserine | 90 | 1.24 |
| 8 | Aspartic acid | 99 | 100.00 |
| 9 | Glutamic acid | 95 | 8.73 |
| 10 | Asparagine | 99 | 17.79 |
| 11 | Lactic | 95 | |
| 12 | Oxalic | 76 | |
| 13 | Malonic | 91 | |
| 14 | Maleic | 78 | |
| 15 | Succinic | 95 | |
| 16 | Fumaric | 99 | |
| 17 | Malic | 94 | |
| 18~27 | Unidentified | | |

[a]: not detected

5) Analysis of Organic acid

Figure 30:
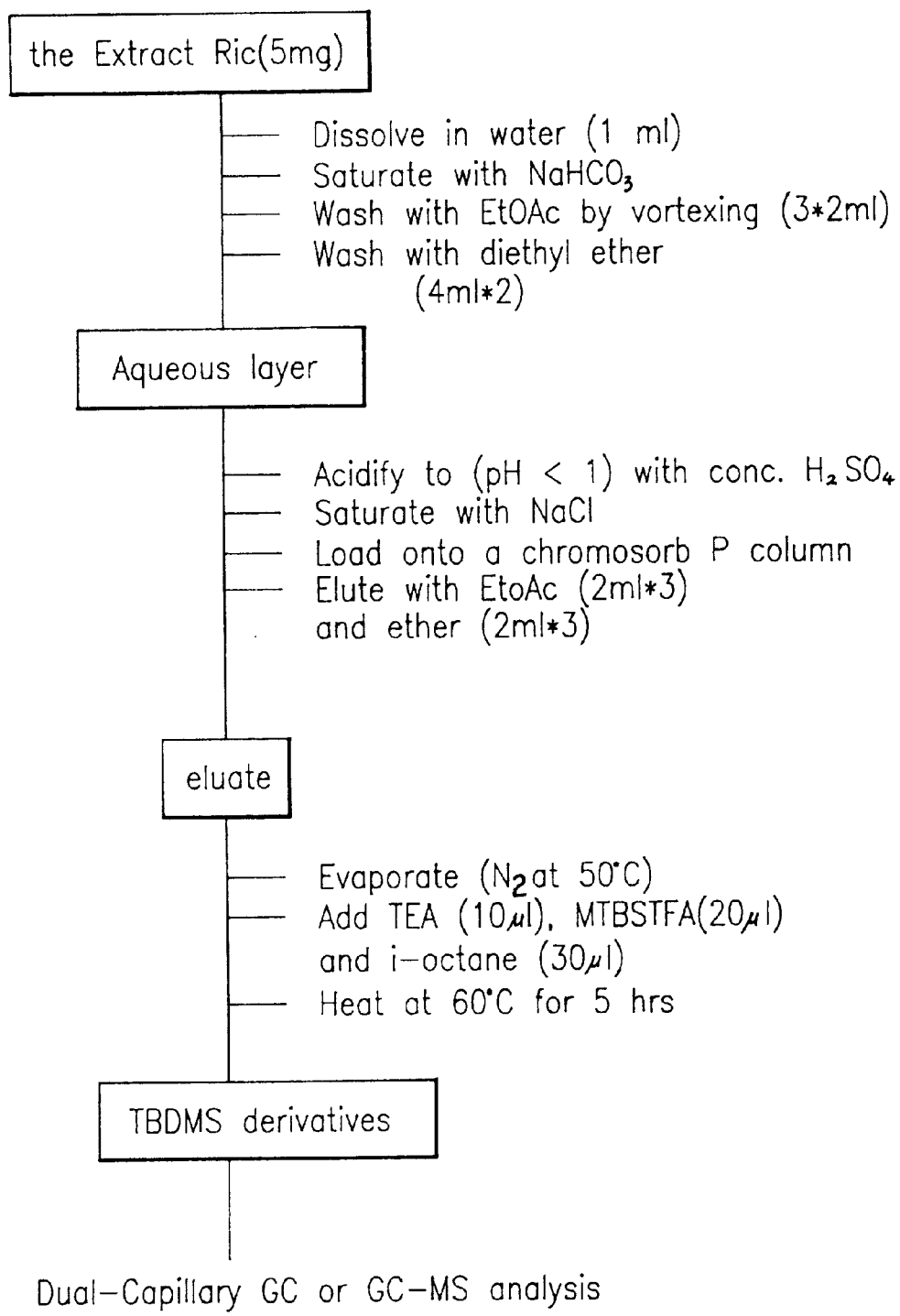
FIG. 30 represents a flow chart for TBDMS derivatization for organic acids from the extract of the present invention.
Figure 31:
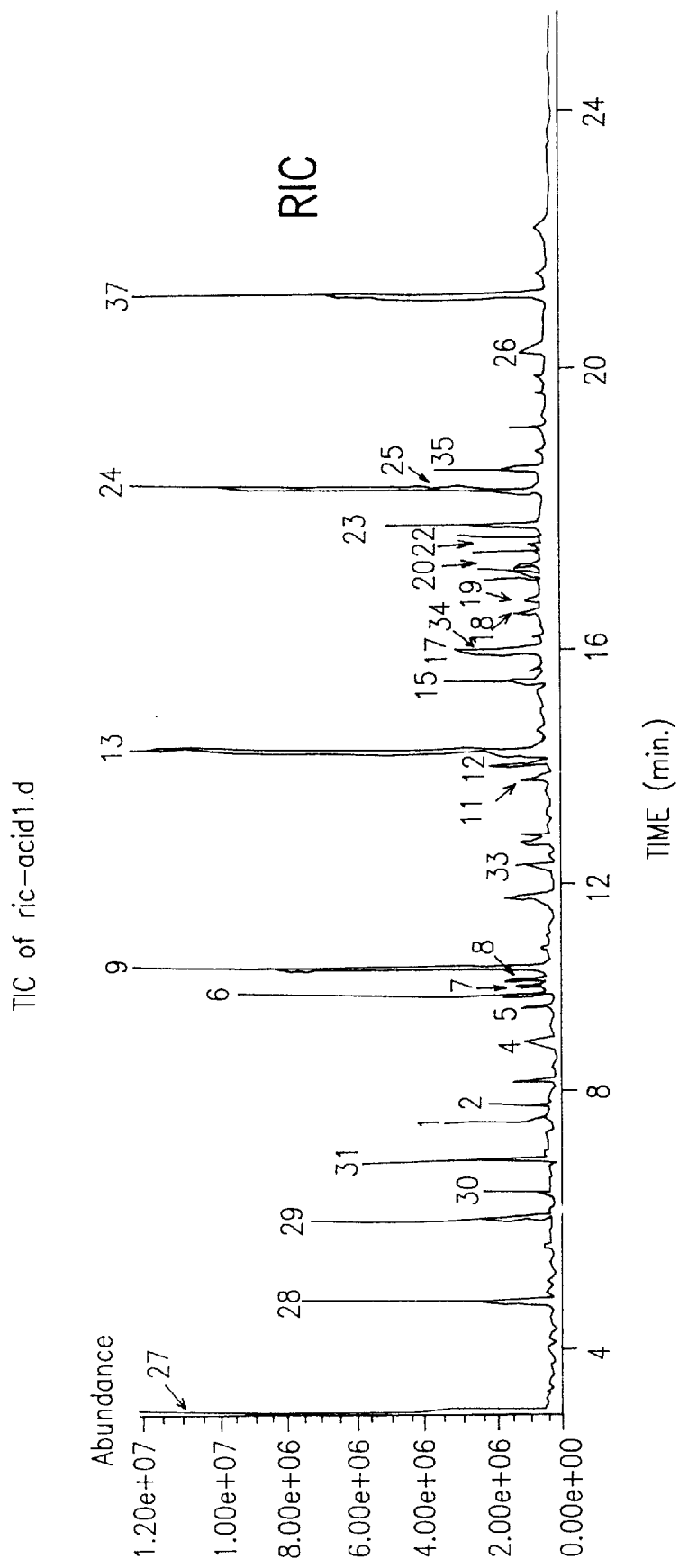
FIG. 31 represents organic acid profiles of the extract as the N(O,S)-isoBOC TBDMS derivatives.

Organic acids were analyzed using gas chromatography (Hewlett Packard GC 5890A). Organic acids were derivatized by tert-butyl-dimethylsilyl (TBDMS) derivatization method using N-methyl-N-(tert.-butyldimethyl-silyl) trifluoroacetamide (MTBSTFA) as shown in FIG. 30. Organic acids were analysed by DB-5 and DB-17 dual-capillary column GC system, and temperature-programmed retention index (RI) of each compound was obtained (FIG. 31). Each compound was identified from RI and mass spectra through screening the library in the GC chemstation (Table 7). 35 peaks were observed in the gas chromatograph. The extract included 35 kinds of organic acids. Among the organic acids identified are lactic acid, glycolic acid, oxalic acid, malonic acid, maleic acid, succinic acid, methylsuccinic acid, fumaric acid, suberic acid, and citric acid.

Operating conditions for GC analysis:
Column: Dual-Capillary Column system (J & W Scientific, Rancho, U.S.A.)
   DB-5 and DB-17 fused silica capillary columns
   30 m×0.25 mm I.D., 0.25 μm df)
Column temp.: 60° C. (2 min.) to 280° C. at 4° C./min.
Injection mode: Split injection mode at 280° C.
Detector: FID at 300° C.
Operating conditions for GC-MS analysis:
Column: HP-1 cross-linked capillary column
   (12 m×0.20 mm I.D., 0.33 μm df)
HP-5 cross-linked capillary column
   (25 m×0.20 mm I.D., 0.33 μm df)
Column temp.: 100° C. (2 min.) to 280° C. at 10° C./min
Injection temperature: Split injection mode at 260° C. (split ratio of 10:1)
Interface temperature: 280° C.
Mass range: 50 to 650 amu at 1.0 n scan/sec.

TABLE 7

Organic acids found in the extract by tbdms. 1 MS library searching

| No. | Compound | Library match quality[%] | Normalized area (%) the extract |
|---|---|---|---|
| 1 | Lactic acid | 95 | 9.63 |
| 2 | Glycolic acid | 95 | 7.52 |
| 3 | Oxalic acid | 76 | n.d.[a] |
| 4 | Malonic acid | 91 | 4.46 |
| 5 | Maleic | 78 | 3.28 |
| 6 | Succinic | 95 | 34.77 |
| 7 | Methylsuccinic | 95 | 2.49 |
| 8 | Citraconic | 70 | 1.16 |
| 9 | Fuamric | 99 | 81.14 |
| 10 | Glutaric | 83 | n.d. |
| 11 | Myristic | 81 | 3.44 |
| 12 | p-Hydroxyphenylacetic | 89 | 6.20 |
| 13 | Malic | 94 | 100.00 |
| 14 | Suberic | 74 | n.d. |
| 15 | Vanillic | 96 | 13.11 |
| 16 | Azelic | 41 | n.d. |
| 17 | Palmatine | 98 | 9.28 |
| 18 | Syringic | 99 | 3.94 |
| 19 | cis-Aconitic | 95 | 3.08 |
| 20 | Gentisic | 43 | 9.05 |
| 21 | 4-Hydroxycinnamic | 86 | n.d. |
| 22 | Stearic | 95 | 7.21 |
| 23 | Protocatechuic | 93 | 17.80 |
| 24 | Ferulic | 99 | 82.27 |
| 25 | p-Hydroxyphenyllactic | 78 | trace |
| 26 | Caffeic | 85 | 3.52 |
| 27~39 | Unidentified | | |

[a]: not detected

EXAMPLE 11

Analysis of Medicinal Components

Figure 32:
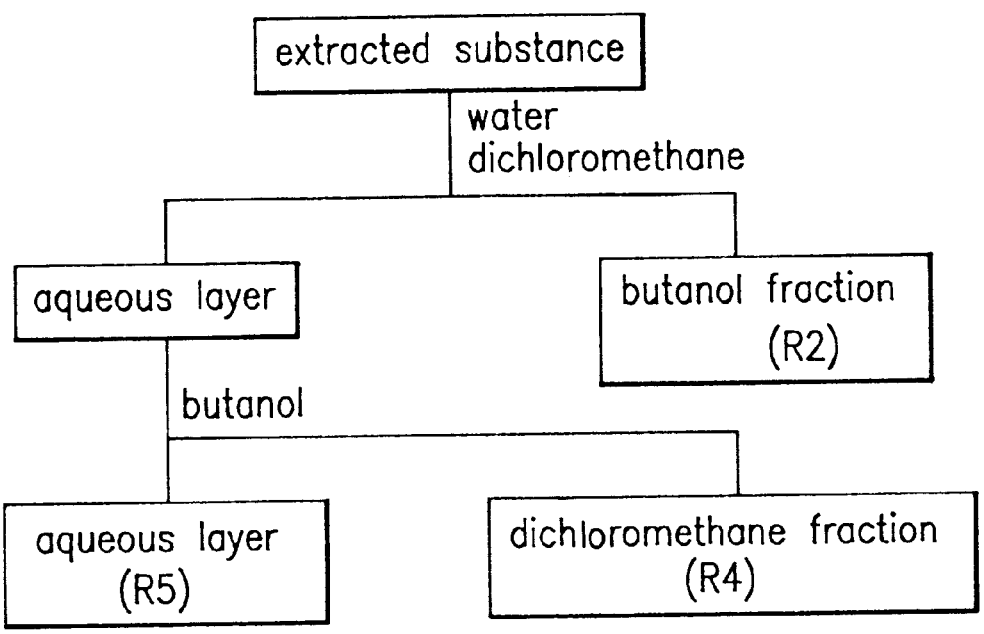
FIG. 32 represents fractionation of the extract by solvent extraction.

The activity of the extracted substance was investigated by extracting medicinal components with various solvents and fractionating them as follows (FIG. 32).

The butanol fraction (R4) showed the best antioxidant activity and anti-HIV effect. The derivatives of berberine, protoberberine, and flavonoids are found in the butanol fraction.

It was reported that protoberberine alkaloids contained in Coptis inhibit the reverse transcriptase of HIV-1 and HIV-2 (Tan, G. T., Miller, J. F., Kinghorn, A. D., Highes, S. H., and Pezzuto, J. M.; HIV-1 and HIV-2 reverse transcriptases: A comparative study of sensitivity to inhibition by selected natural products. Biochem. Biophys. Res. Commun. 185(1): 370–278, 1992.) The anti-HIV effect is in order of jatrorrhizine chloride>berberine chloride>coptisine chloride. These materials were contained in the extracted substance of the invention and when they show anti-HIV effect, antioxidative compounds (flavonoids) are considered to increase the effect (Ono, K., Nakane, H., Fukushima, M., Chermann, J. C., Barre, S. F.; Differential inhibitory effects of various flavonoids on the activities of reverse transcriptase and cellular DNA and RNA polymerase. Eur. J. Biochem. 190 (3): 469–176, 1990).

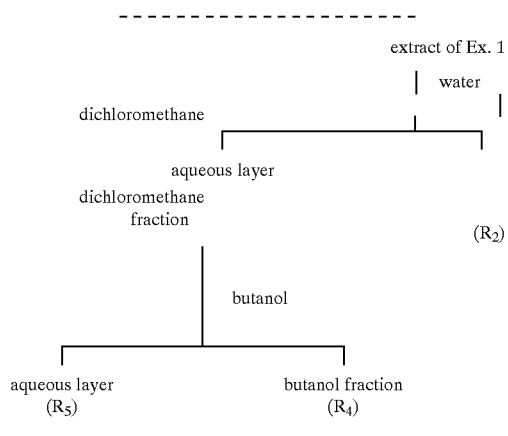

We consider that the presence of antioxidants in the extract is increasing the efficacy of the berberine and protoberberine alkaloids as HIV reverse transcriptase inhibitors.

EXAMPLE 12

Acute Toxicity Test

Both sexes of Sprague-Dawley rats and ICR mice were obtained at 5 weeks of age. Twenty-five male and female rats were divided into five groups according to the dose of the extract. Twenty male and female mice were divided into four groups. The extract dissolved with water for injection and adjusted to pH 7.4, was administered once subcutaneously. The dose range of the extract injected was 100–500 mg/kg body weight in rat, and 125–148.5 mg/kg in mice.

Results of acute toxicity tests (1) Mortalities and $LD_{50}$

When the extract is administered, two and three male rats at the group of 1000 mg/kg B.W. were dead at 2 hours and 24 hours, respectively. In each group of 840.9 mg/kg B.W. and 707.11 mg/kg B.W. two rats were dead at 24 hours. In female rats at 1000 mg/kg B.W., two and three were dead at 2 hours and 24 hours, respectively. At the doses of 840.9 mg/kg B.W. and 707.11 mg/kg B.W., two and three were dead at 24 hours, respectively.

Mice were more sensitive than rats. In males at the highest amount, 148.65 mg/kg B.W., one and four were dead at 6 hour and 24 hours, respectively. At the groups of 140.3 mg/kg B.W. and 132.43 mg/kg B.W., three and two were dead at 24 hours, respectively, and no death was observed at a dose of 125 mg/kg B.W. In female mice at the highest dose, 210.22 mg/kg B.W., two were dead at 4 hours and one additional death at each of 5 hours, 6 hours, and 24 hours. At 176.78 mg/kg B.W., one died at each of 5 hours and 6 hours, and three at 24 hours, resulting in all of the mice being deceased. At doses of 148.65 mg/kg B.W. and 125 mg/kg B.W. three and one mice were dead at 24 hours, respectively. There was no death in the group receiving a dose of 105.11 mg/kg B.W.

$LD_{50}$ of rat, therefore, in males was 795.12 mg/kg B.W. and in females 771.11 mg/kg B.W.; $LD_{50}$ of mice, in males was 136.31 mg/kg B.W. and in females 140.76 mg/kg B.W.

(2) Clinical symptoms

Both rats and mice, for both males and females, showed depression and decreased activity after treatment with the extract, and these symptoms were dose-dependent. Every death was observed within a day, and surviving animals recovered after the second day. There were no typical clinical symptoms by the third day.

(3) Change of body weight

There were no significant changes observed.

(4) Autopsy findings

There were no abnormal changes at autopsy.

(5) Pathological findings

Subcutaneous administration of the extract induced distinctive renal changes in rat and mouse. Profound necrosis and diffused deformation of renal tubules were observed. Renal tubules were filled up with fibrinous cast, and same material was observed in Bowman's space. Especially, tuft and capular membrane of glomerulus was attached, and crescent was enlarged enough to press tuft in some glomerulus. Furthermore, collagen-like materials were expressed in Bowman's space and tuft in Bowman's space disappeared in some cases.

Although the degree of change in liver was not as clear as in kidney, activation of Kupffer cells was observed, and changes in nucleui were clear; margination of chromatin, different size of nuclei were observed. Furthermore, a number of mitotic phase nuclei were observed.

EXAMPLE 13

Subacute Toxicity Test

Both sexes of Sprague-Dawley rats and ICR mice were obtained at 5 weeks of age. Forty male and female rats were divided into four groups according to the dose of the extract. Forty male and female mice were divided into four groups. The extract, dissolved in water for injection and adjusted to pH 7.4, was administered once subcutaneously. Various doses of the extract were injected 0, 62.5 (low), 125 (mid), 250 (high) mg/kg B.W. in rat, and 0, 12.5 (low) 25 (mid), 50 (high) mg/kg in mice.

Tested items were clinical signs, feed consumption, water consumption, body weights, opthalmoscopy, urine analysis, hematology and blood biochemistry, autopsy, organ weights, and histopathological examination.

Results of subacute toxicity tests (1) Clinical signs and mortalities

All groups of rats and mice showed depression and sweating at initial phase. Two or three female rats died each day at the high dose. In the case of male rats, one of them died at day 5 and one at day 24 at the high dose. One of male mice died at day 14 at the high and at mid dose, and three of female mice died at day 14 at the high dose of the extract.

(2) Change of body weight

Significant decrease of body weight in the high dose group of female rats was observed from one week after administration kof the extract. In the mid and low dose group of rats, body weight was decreased after 3 weeks and 4 weeks. There was no change in body weight in mice.

(3) Consumption of food and water

There were not changes compare to control group.

(4) Opthalmoscopy and urine analysis

There were not clear differences among all groups.

(5) Hematological tests

Abbreviations

RBC: erythrocyte count

MCHC: mean corpuscular hemoglobin concentration

MCH: mean corpuscular hemoglobin

PLT: platelet count

MPV: mean platelet volume

RDW: red cell distribution width

ALT: alanine transaminase

AST: aspartate transaminase

ALP: alkaline phosphatase

BUN: blood urea nitrogen

MPV was decreased in the mid dose group of male mice, but not in female. Red blood cell count, Hemoglobin, MCH, MCHC, RDW, PLT, were significantly changed ($p<0.05$) in the high dose group of female rats, but not in the low dose group.

(6) Blood biochemistry ALT and AST were increased in the mid dose group of male mice, but sodium, AST, glucose, total protein, potassium, blood urea nitrogen (BUN), albumin were changed significantly in female. Sodium and BUN were changed in high dose group of male rats, and sodium bilirubin, ALP, BUN, albumin were changed ($p<0.05$) in the high dose group females, but not in the low dose group.

(7) Autopsy findings

There were not any abnormal findings. One female rat of the high dose group had milky circular spots in liver.

(8) Weight of organs

No changes of heart or brain weight were observed in either mice or rats.

(9) Histopathological findings

Tubular necrosis, glomerulonephritis, and vacuolation in liver were observed in male mice, female mice showed interstitial nephritis including above symptoms. Rats showed similar symptoms in both of male and female. Mitosis in liver was typically found, and extramedullary hematopoiesis in liver and spleen also frequently observed. Other organs were not changed compared to controls.

What is claimed is:

1. A composition comprising an extract from a mixture of the non-fat starches of *Ricini semen* and a root of a Coptis species, wherein said extract comprises berberine and at least one flavanoid, and wherein said extract is substantially free of the protein ricin and the alkaloid ricinine.

2. The composition of claim 1, wherein said extract further comprises a protein component of molecular weight approximately 10 kilodaltons as measured by electrophoresis.

3. The composition of claim 2, wherein said protein component consists essentially of glycine, pyroglutamic acid, glutamic acid, asparagine, serine, homoserine, and aspartic acid.

4. The composition of claim 3, wherein the ratio of aspartic acid to asparagine to glutamic acid, to serine to pyroglutamic acid to homoserine to glycine is 100:17.8:8.7:3.3:2.6:1.2:1.2.

5. The composition of claim 3, wherein said extract further comprises the organic acids malic acid, ferulic acid, fumaric acid and succinic acid.

6. The composition of claim 5, wherein the ratio of malic acid to ferulic acid to fumaric acid to succinic acid is 100:82.3:81.1:34.8.

7. The composition of claim 3, wherein said extract further comprises the organic acids malic acid, ferulic acid, fumaric acid, succinic acid, protocatechuic acid, vanillic acid, lactic acid, palmatine, glycolic acid, stearic acid, syringic acid, cis-aconitic acid and methylsuccinic acid.

8. The composition of claim 7, wherein the ratio of malic acid to ferulic acid to fumaric acid to succinic acid to protocatechuic acid to vanillic acid to lactic acid to palmatine to glycolic acid to stearic acid to syringic acid to cis-aconitic acid to methylsuccinic acid is 100:82.3:81.1:34.8:17.8:13.1: 9.6:9.3:7.5:7.2:3.9:3.1:2.5.

9. The composition of claim 1, wherein said extract further comprises the organic acids malic acid, ferulic acid, fumaric acid and succinic acid.

10. The composition of claim 9, wherein said extract further comprises the organic acids protocatechuic acid, vanillic acid, lactic acid, palmatine, glycolic acid, stearic acid, syringic acid, cis-aconitic acid and methylsuccinic acid.

11. The composition of claim 10, wherein the ratio of malic acid to ferulic acid to fumaric acid to succinic acid to protocatechuic acid to vanillic acid to lactic acid to palmatine to glycolic acid to stearic acid to syringic acid to cis-aconitic acid to methylsuccinic acid is 100:82.3:81.1:34.8:17.8:13.1: 9.6:9.3:7.5:7.2:3.9:3.1:2.5.

12. The composition of claim 9, wherein the ratio of malic acid to ferulic acid to fumaric acid to succinic acid is 100:82.3:81.1:34.8.

* * * * *